United States Patent
Jordan et al.

(10) Patent No.: US 12,350,517 B2
(45) Date of Patent: *Jul. 8, 2025

(54) IMAGE-GUIDED RADIATION TREATMENT WITH IMAGING DATA USING IMAGING RADIATION AT DIFFERENT ENERGY LEVELS

(71) Applicant: Accuray Incorporated, Sunnyvale, CA (US)

(72) Inventors: Petr Jordan, Redwood City, CA (US); Andriy Myronenko, San Mateo, CA (US); Jay B. West, Mountain View, CA (US); Calvin R. Maurer, San Jose, CA (US); Prashant Chopra, Foster City, CA (US); Anuj K Purwar, Pleasanton, CA (US); Christopher A. Janko, Redwood City, CA (US)

(73) Assignee: Accuray Incorporated, Sunnyvale, CA (US)

( * ) Notice: Subject to any disclaimer, the term of this patent is extended or adjusted under 35 U.S.C. 154(b) by 391 days.

This patent is subject to a terminal disclaimer.

(21) Appl. No.: 17/520,498

(22) Filed: Nov. 5, 2021

(65) Prior Publication Data

US 2022/0054860 A1 Feb. 24, 2022

Related U.S. Application Data

(63) Continuation of application No. 17/083,051, filed on Oct. 28, 2020, now Pat. No. 11,185,715, which is a
(Continued)

(51) Int. Cl.
*A61N 5/10* (2006.01)
*A61B 6/00* (2024.01)
(Continued)

(52) U.S. Cl.
CPC .......... *A61N 5/1037* (2013.01); *A61B 6/482* (2013.01); *A61N 5/1049* (2013.01); *A61B 6/025* (2013.01);
(Continued)

(58) Field of Classification Search
CPC ......... A61B 6/025; A61B 6/032; A61B 6/482; A61B 6/583; A61B 6/4035; A61B 6/5223;
(Continued)

(56) References Cited

U.S. PATENT DOCUMENTS 4,965,726 A   10/1990  Heuscher et al.
6,683,934 B1 * 1/2004  Zhao ................. A61B 6/032
                                                     378/4
(Continued)

OTHER PUBLICATIONS

International Preliminary Report on Patentability and Written Opinion of the International Searching Authority for International Application No. PCT/US2012/044513, The International Bureau of WIPO, Apr. 22, 2014, 11 pages, Geneva, Switzerland.
(Continued)

*Primary Examiner* — Chih-Cheng Kao
(74) *Attorney, Agent, or Firm* — Womble Bond Dickinson (US) LLP

(57) ABSTRACT

A method of image-guided radiation treatment is described. The method includes processing a first and second sets of image data to generate an enhanced image, wherein the enhanced image comprises a combination of the first and second sets of image data, wherein part or all of the image data comprises a target of a patient. The method also includes registering the enhanced image with another image to obtain a registration result and tracking the target using the registration result to generate tracking information. The method also includes directing treatment delivery to the
(Continued)

target based on the tracking information obtained from the enhanced image.

22 Claims, 14 Drawing Sheets

Related U.S. Application Data continuation of application No. 16/679,686, filed on Nov. 11, 2019, now Pat. No. 10,843,010, which is a continuation of application No. 15/208,049, filed on Jul. 12, 2016, now Pat. No. 10,485,989, which is a continuation of application No. 13/536,737, filed on Jun. 28, 2012, now Pat. No. 9,415,240.

(60) Provisional application No. 61/550,309, filed on Oct. 21, 2011.

(51) Int. Cl.
  *A61B 6/02* (2006.01)
  *A61B 6/58* (2024.01)
  *A61B 6/40* (2024.01)

(52) U.S. Cl.
  CPC ........... *A61B 6/4035* (2013.01); *A61B 6/5223* (2013.01); *A61B 6/583* (2013.01); *A61N 2005/1061* (2013.01); *A61N 2005/1062* (2013.01); *A61N 5/1067* (2013.01); *A61N 5/1083* (2013.01)

(58) Field of Classification Search
  CPC .. A61B 6/1049; A61N 5/1037; A61N 5/1049; A61N 5/1061; A61N 5/1067; A61N 5/1083; A61N 2005/1061; A61N 2005/1062
  See application file for complete search history.

(56) References Cited

U.S. PATENT DOCUMENTS

| | | |
|---|---|---|
| 7,522,779 B2 | 4/2009 | Fu et al. |
| 7,532,705 B2 | 5/2009 | Yin et al. |
| 7,831,073 B2 | 11/2010 | Fu et al. |
| 7,869,862 B2 | 1/2011 | Seppi et al. |
| 8,311,185 B2 | 11/2012 | Seppi et al. |
| 10,485,989 B2 * | 11/2019 | Jordan ............ A61N 5/1049 |
| 10,843,010 B2 * | 11/2020 | Jordan ............ A61B 6/482 |
| 11,185,715 B2 * | 11/2021 | Jordan ............ A61B 6/482 |
| 2002/0191751 A1 | 12/2002 | Bogatu et al. |
| 2003/0026758 A1 * | 2/2003 | Baker ............ A61N 5/1049 424/9.1 |
| 2003/0048868 A1 * | 3/2003 | Bailey ............ A61B 6/032 378/65 |
| 2003/0233039 A1 | 12/2003 | Shao et al. |
| 2004/0068169 A1 | 4/2004 | Mansfield et al. |
| 2004/0101086 A1 | 5/2004 | Shao et al. |
| 2004/0131150 A1 | 7/2004 | Pankratov et al. |
| 2005/0020869 A1 | 1/2005 | Hainfeld et al. |
| 2005/0080332 A1 | 4/2005 | Shiu et al. |
| 2006/0002615 A1 | 1/2006 | Fu et al. |
| 2006/0176997 A1 | 8/2006 | Dilmanian et al. |
| 2006/0182326 A1 * | 8/2006 | Schildkraut ....... A61N 5/1049 378/65 |
| 2007/0003123 A1 * | 1/2007 | Fu ................. G06T 7/38 604/20 |
| 2007/0055144 A1 * | 3/2007 | Neustadter ....... A61N 5/1049 600/425 |
| 2007/0158573 A1 | 7/2007 | Deych |
| 2007/0184955 A1 | 8/2007 | Allison |
| 2008/0061395 A1 | 3/2008 | Tkaczyk et al. |
| 2008/0187095 A1 | 8/2008 | Boone et al. |
| 2008/0232546 A1 | 9/2008 | Stierstorfer |
| 2008/0240357 A1 | 10/2008 | Jabri et al. |
| 2008/0260101 A1 | 10/2008 | Oreper |
| 2009/0003528 A1 | 1/2009 | Ramraj et al. |
| 2009/0122953 A1 | 5/2009 | Imai |
| 2009/0135994 A1 | 5/2009 | Yu et al. |
| 2009/0220043 A1 | 9/2009 | Nishide et al. |
| 2009/0274269 A1 | 11/2009 | Foland et al. |
| 2009/0283682 A1 | 11/2009 | Star-Lack et al. |
| 2009/0290680 A1 | 11/2009 | Turner et al. |
| 2010/0020920 A1 | 1/2010 | Mertelmeier |
| 2010/0080354 A1 | 4/2010 | Fu et al. |
| 2010/0102242 A1 | 4/2010 | Burr et al. |
| 2010/0111388 A1 | 5/2010 | Seppi et al. |
| 2010/0119035 A1 | 5/2010 | Karch |
| 2010/0220835 A1 | 9/2010 | Gibson et al. |
| 2010/0220912 A1 | 9/2010 | Bruder et al. |
| 2010/0232572 A1 | 9/2010 | Nord et al. |
| 2010/0278296 A1 | 11/2010 | Edic et al. |
| 2010/0329413 A1 | 12/2010 | Zhou et al. |
| 2011/0210261 A1 | 9/2011 | Maurer, Jr. |
| 2012/0008734 A1 | 1/2012 | Thomson et al. |
| 2012/0008735 A1 | 1/2012 | Maurer et al. |

OTHER PUBLICATIONS

International Search Report for International Application No. PCT/US2012/044513, European Patent Office, Feb. 22, 2013, 7 pages, Rijswijk, The Netherlands.

Written Opinion of the International Searching Authority for International Application No. PCT/US2012/044513, European Patent Office, Feb. 22, 2013, 10 pages, Munich, Germany.

Invitation to Pay Additional Fees and, Where Applicable, Protest Fee for International Application No. PCT/US2012/044513, European Patent Office, Oct. 17, 2012, 8 pages, Rijswijk, The Netherlands.

International Electrotechnical Commission (2009). "International Standard (IEC 60601-2-1), Medical Electrinical Equiment" 132 pages.

Meijering et al., Image Registration for Digital Subtraction Angiography, Apr. 1999, International Journal of Computer Vision, vol. 31, No. 2/3, p. 227, 228, 230.

Lindhardt, Digital Breast Tomosynthesis, Jun. 2010, Siemens Healthcare white paper, p. 3, 5.

Debevec, et al., Recovering High Dynamic Range Radiance Maps from Photographs, available at http://www.pauldebevec.com/Research/HDR/debevec-siggraph97.pdf (last visited Oct. 24, 2012), Aug. 1997.

Jakubek, Jan, Beam Hardening Correction, available at http://aladdin.utef.cvut.cz/ofat/methods/BeamHardening/BeamHardening.html (last visited Oct. 24, 2012).

Basic Physics of Nuclear Medicine/Dual-Energy Absorptiometry, available at http://en.wikibooks.org/wiki/Basic.sub.-Physics.sub.-of.sub.-Nuclear.s-ub.-Medicine/Dual-Energy.sub.-Absorptiometry (last visited Oct. 24, 2012), Last updated on Apr. 2013.

Delorme et al., Three-Dimensional Modelling and Rendering of the Human Skeletal Trunk from 2D Radiographic Images, Oct. 1999, IEEE Proceedings of the Second International Conference on 3-D Digital Imaging and Modeling, p. 497-499.

Graves et al., Design and evaluation of a variable aperture collimator for conformal radiotherapy of small animals using a microCT scanner, Nov. 2007, Med. Phys. vol. 34, No. 11, p. 4359, 4360.

Mu et al., Does electron and proton therapy reduce the risk of radiation induced cancer after spinal irradiation for childhood medulloblastoma? A comparative treatment planning study, Jun. 2007, Acta Oncologica, vol. 44, p. 554-556.

Shkumat et al., Optimization of image acquisition techniques for dual-energy imaging of the chest, Oct. 2007, Med. Phys. vol. 34, No. 10, p. 3904, 3905, 3907-3909, 3911.

\* cited by examiner

IMAGE-GUIDED RADIATION TREATMENT WITH IMAGING DATA USING IMAGING RADIATION AT DIFFERENT ENERGY LEVELS

RELATED APPLICATIONS

This application is a continuation of U.S. patent application Ser. No. 17/083,051, filed on Oct. 28, 2020, which is a continuation of U.S. patent application Ser. No. 16/679,686, filed on Nov. 11, 2019, now issued as U.S. Pat. No. 10,843,010 on Nov. 4, 2020, which is a continuation of U.S. patent application Ser. No. 15/208,049, filed on Jul. 12, 2016, now issued as U.S. Pat. No. 10,485,989 on Nov. 26, 2019, which is a continuation of U.S. patent application Ser. No. 13/536,737, filed on Jun. 28, 2012, now issued as U.S. Pat. No. 9,415,240 on Aug. 16, 2016, which claims the priority to U.S. Provisional Patent Application No. 61/550,309, filed Oct. 21, 2011, the entire contents of which are incorporated herein by reference.

TECHNICAL FIELD

This application relates to apparatus for generating multi-energy x-ray images and systems and methods for using multi-energy x-ray images in image-guided radiation therapy.

BACKGROUND

Oncology is the branch of medicine directed to the study of the development, diagnosis, treatment, and prevention of tumors. A tumor is an abnormal growth of tissue serving no physiological function. A tumor may be malignant (cancerous) or benign. A malignant tumor may exhibit uncontrolled, progressive multiplication of cells and spread cancerous cells to other parts of the body (metastasizes) through blood vessels or the lymphatic system. A benign tumor does not metastasize, but can still be life-threatening if it impinges on critical body structures such as nerves, blood vessels, and organs.

Radiosurgery and radiotherapy are radiation treatment systems that use external radiation beams to treat tumors and other lesions by delivering a prescribed dose of radiation (e.g., x-rays, protons, or gamma rays) to a target volume (region of interest, or ROI) while minimizing radiation exposure to the surrounding tissue. The object of both radiosurgery and radiotherapy is the destruction of abnormal tissue while sparing healthy tissue and critical structures. Radiotherapy is characterized by a low radiation dose per treatment and many treatments (e.g., 30 to 45 days of treatment). Radiosurgery is characterized by a relatively high radiation dose to a tumor in one, or at most a few, treatments. In both radiotherapy and radiosurgery, the radiation dose is delivered to the tumor site from multiple angles. As the angle of each radiation beam is different, each beam passes through a different area of healthy tissue on its way to the tumor. As a result, the cumulative radiation dose at the tumor is high, while the average radiation dose to the surrounding healthy tissue is low. Unless specified otherwise, radiosurgery and radiotherapy are used interchangeably in the present application.

Radiation treatment systems may be used together with an imaging system for image-guided radiation therapy (IGRT). The imaging system acquires in-treatment images, e.g., x-ray, ultrasound, CT, or PET, that may be used to for patient set up and in some instances (e.g., Accuray Incorporated's CyberKnife® Radiosurgery System) guide the radiation delivery procedure and track in-treatment target motion. Target motion tracking may be accomplished by correcting for differences in target position by acquiring and registering intratreatment images with reference images, known as digitally reconstructed radiographs (DRRs), rendered from a pre-treatment computed tomography (CT) scan, which may otherwise be known as the treatment planning image.

Previously-known IGRT systems use imaging systems that generate single energy x-ray images during treatment. Such systems suffer, however, from a variety of drawbacks. For example, x-ray attenuation characteristics are dependent on x-ray energy and thus a single energy x-ray image may have limited differentiation ability for certain materials. An x-ray image generated using a low x-ray energy (e.g., ~50-100 kV) will display significant attenuation in soft tissue and radio-opaque objects such as skeletal structures, fiducials, and contrast agents. Conversely, an x-ray image generated using a high x-ray energy (e.g., ~100 kV-6 MV, preferably 100-150 kV) will display less attenuation of soft tissue than a low x-ray energy image, but still significant attenuation in radio-opaque objects such as skeletal structures, contrast agents, and fiducials.

In view of the above-noted drawbacks of previously-known systems, it would be desirable to provide apparatus and methods for generating x-ray images with increased discrimination between soft tissue and radio-opaque objects.

It further would be desirable to provide systems and methods for processing and using such x-ray images in image-guided radiation therapy.

DETAILED DESCRIPTION

This disclosure relates to apparatus for generating multi-energy x-ray images and systems and methods for processing and using multi-energy x-ray images in image-guided radiation therapy. Advantageously, x-rays generated at an energy level within a low energy range (e.g., ~50-100 kV) may be enhanced with x-rays generated at an energy level within a high x-ray energy range (e.g., ~100 kV-6 MV, preferably 100-150 kV) to provide x-ray images having high definition for images of soft tissue, and radio-opaque objects such as skeletal structures, fiducials, and contrast agents. Moreover, x-rays generated within the low energy range may be enhanced with x-rays generated within the high x-ray energy range in a weighted manner to provide x-ray images without soft tissue or, alternatively, x-rays images without radio-opaque objects. The enhanced x-ray images may be used for enhanced target tracking and positioning for image-guided radiation therapy.

Figure 1:
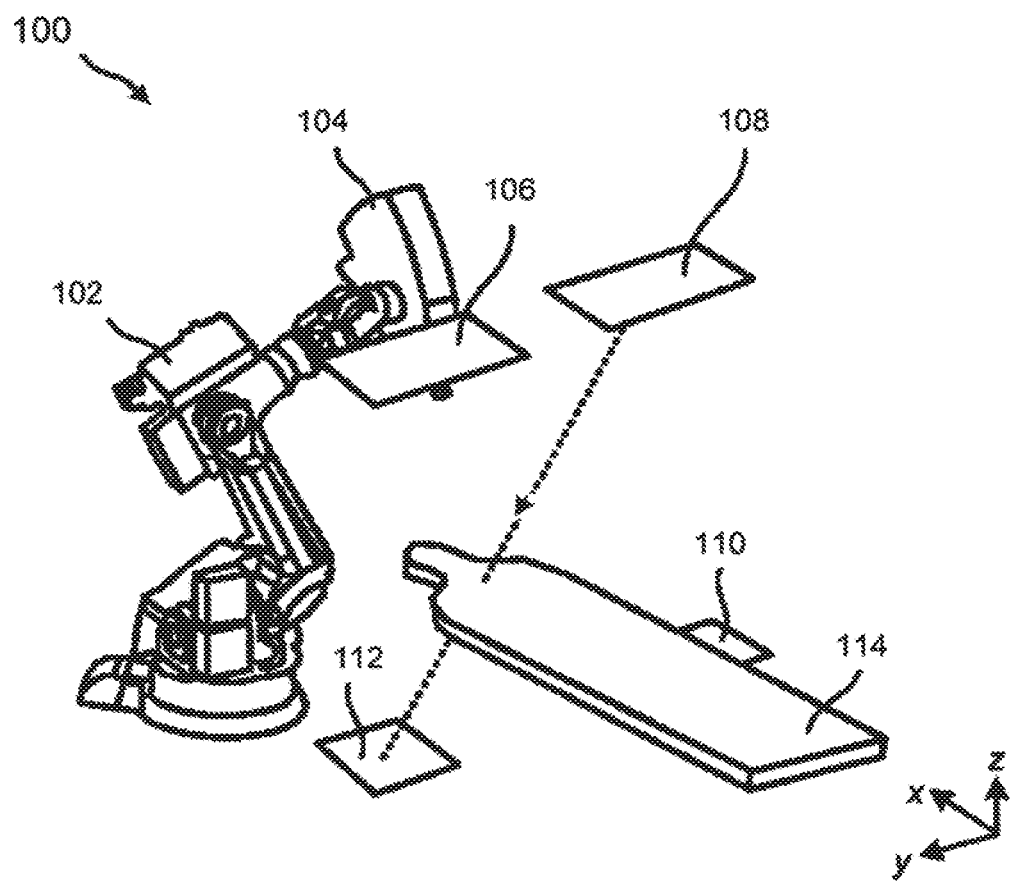
FIG. 1 illustrates a perspective view of a previously-known image-guided radiation therapy (IGRT) system.

FIG. 1 illustrates a perspective view of a previously-known image-guided radiation therapy (IGRT) system 100. IGRT system 100 includes articulated robot arm 102, MV radiation source 104, x-ray sources 106 and 108, x-ray detectors 110 and 112, and treatment table 114. An example of IGRT system 100 is a CYBERKNIFE® Robotic Radiosurgery System available from Accuray, Incorporated, Sunnyvale, California.

In FIG. 1, MV radiation source 104 is configured to generate treatment radiation beams, e.g., x-ray photon, electron, or proton beams, at a target volume, e.g., a tumor, within a patient. MV radiation source 104 generally includes a linear accelerator (LINAC). MV radiation source 104 is mounted on the end of articulated robot arm 102 to provide multiple (e.g., 5 or more) degrees of freedom of motion in order to position MV radiation source 104 to irradiate tumorous tissue with highly-collimated beams delivered from many angles in an operating volume (e.g., sphere) around the patient. Treatment may involve beam paths with a single isocenter, multiple isocenters, or with a non-isocentric approach (e.g., the beams need only intersect with the targeted tumor mass and do not necessarily converge on a single point, or isocenter, within the target region). Treatment can be delivered in either a single session (mono-fraction), in a small number of sessions (hypo-fractionation), or in a large number (30-40) of sessions (standard fractionation) as determined during treatment planning.

IGRT system 100 has a real-time imaging system that includes first x-ray source 106, second x-ray source 108, first x-ray detector 110, and second x-ray detector 112. First x-ray source 106 is paired with first x-ray detector 110 to establish a first "channel" of a stereoscopic x-ray imaging system, and second x-ray source 108 is paired with second x-ray detector 112 to establish a second "channel." During radiation treatment, first and second x-ray sources 106 and 108 emit single-energy x-ray imaging radiation that travels through a patient and treatment table 114 and is received by first and second x-ray detectors 110 and 112, respectively. The in-treatment, single-energy x-ray images are used to set up and guide the treatment radiation delivery procedure and track in-treatment target motion. The target is tracked by correcting for differences in target position in the in-treatment, single-energy x-ray images and registering them with reference images, known as digitally reconstructed radiographs (DRRs), rendered from a pre-treatment computed tomography (CT) scan.

Applicants have concluded that higher definition in-treatment x-ray images may be generated by providing apparatus for generating multi-energy x-ray images. Further, applicants have discovered systems and methods for processing and using multi-energy x-ray images in image-guided radiation therapy.

Apparatus for Generating Multi-Energy X-Ray Images

Figure 2:
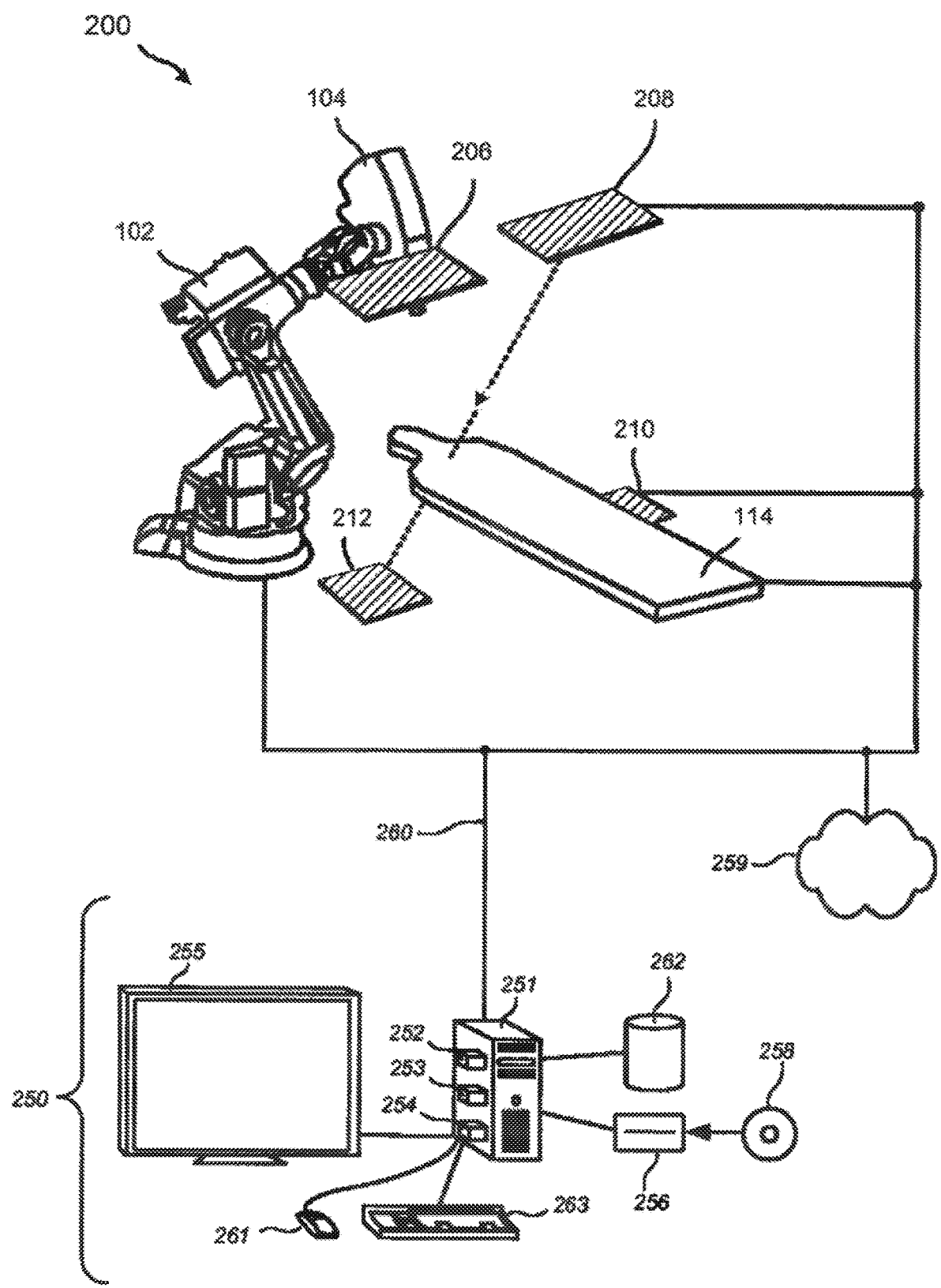
FIG. 2 illustrates a perspective view of an IGRT system and a schematic diagram of a computer system in accordance with the principles of the present invention.

FIG. 2 illustrates a perspective view of image-guided radiation therapy (IGRT) system 200 and a schematic diagram of computer system 250 in accordance with the principles of the present invention. IGRT system 200 includes articulated robot arm 102, MV radiation source 104, x-ray sources 206 and 208, x-ray detectors 210 and 212, and treatment table 114. Articulated robot arm 102, MV radiation source 104, and treatment table 114 may be conventional and, thus, are not described in detail.

Advantageously, IGRT system 200 has a real-time imaging system configured to generate multi-energy x-ray images. The real-time imaging system includes first x-ray source 206, second x-ray source 208, first x-ray detector 210, and second x-ray detector 212. First x-ray source 206 is paired with first x-ray detector 210 to establish a first "channel" of a stereoscopic x-ray imaging system, and second x-ray source 208 is paired with second x-ray detector 212 to establish a second "channel." During radiation treatment, first and second x-ray sources 206 and 208 emit imaging radiation that travels through part or all of a patient and treatment table 114 and is received by first and second x-ray detectors 210 and 212, respectively.

First and second x-ray sources 206 and 208 may include kV x-ray tube technology, x-ray source array technology, broad energy technology, or other suitable x-ray source technology. X-ray source array refers to a source of x-rays comprising a plurality of spatially distinct, electronically controlled x-ray emitters or emission spots (focal spots) that are addressable on at least one of an individual or groupwise basis such as an x-ray source array available from Triple Ring Technologies (Newark, California) or XinRay Systems (Research Triangle Park, North Carolina). First and second x-ray detectors 210 and 212 may be amorphous silicon detectors or other suitable detectors capable of producing high-quality two-dimensional x-ray images during an IGRT. X-ray sources 206 and 208 may be mounted in or near the ceiling of a treatment vault, while x-ray detectors 210 and 212 may be mounted in or near the floor of the treatment vault as illustrated, although the scope of the preferred embodiments is not limited thereto. It should be noted that although the real-time imaging system of IGRT system 200 is illustrated as having two x-ray sources and two x-ray detectors, IGRT system 200 is not limited thereto. For example, IGRT system 200 may have one, three, four or more x-ray sources and one, three, four or more x-ray detectors.

In accordance with one embodiment, first x-ray source 206 is configured to emit imaging radiation at an energy level within a low x-ray energy (e.g., ~50-100 kV). An x-ray generated from low energy radiation has significant attenuation in soft tissue and radio-opaque objects and the resulting image will display soft tissue in conjunction with radio-opaque objects. In this embodiment, second x-ray source 208 is configured to emit radiation at an energy level within a high x-ray energy range (e.g., ~100-150 kV). An x-ray generated from high energy radiation has greater attenuation in radio-opaque objects, but little attenuation in soft tissue, and the resulting image will display primarily radio-opaque objects without soft tissue.

After the emitted radiation travels through the patient, first x-ray detector 210 receives the low energy imaging radiation and second x-ray detector 212 receives the high energy imaging radiation. The received low and high energy imaging radiation then may be processed at computer system 250, described further below, to generate first and second sets of image data using suitable software and to produce real-time x-ray images having enhanced definition for radio-opaque objects and soft tissue. In one embodiment, first and second x-ray detectors are energy-binning photon counting detectors.

In an alternative embodiment, first and second x-ray sources 206 and 208 may each alternate between low energy and high energy emission modes during respective periodic imaging cycles. In one embodiment, first and second x-ray sources 206 and 208 may be in-phase with each other (i.e., both emitting at low energy, then both emitting at high energy, etc.), while for another embodiment, first and second x-ray sources 206 and 208 may be out of phase with each other (i.e., one emitting at low energy while the other emits at high energy).

In accordance with another aspect of the present invention, the real-time imaging system of IGRT system 200 may be configured to provide multi-energy stereoscopic tomosynthesis images. X-ray tomosynthesis refers to the process of acquiring a number of two-dimensional x-ray projection images of a target volume using x-rays that are incident upon the target volume at a respective number of different angles, followed by the mathematical processing of the two-dimensional x-ray projection images to yield a set of one or more tomosynthetic reconstructed images representative of one or more respective slices of the target volume, wherein the number of x-ray projection images is less than that in a set that would be required for CT image reconstruction, and/or the number or range of incident radiation angles is less than would be used in a CT imaging procedure.

In this embodiment, first and second x-ray source-detector pairs (206/210, 208/212) are positioned to acquire tomosynthesis projection images over first and second non-overlapping projection angle ranges. First and second sets of tomosynthesis projection images of the target volume are acquired at distinct first and second x-ray energy levels, respectively (e.g., 80 kV and 140 kV), using the respective first and second x-ray tomosynthesis source-detector pairs.

The first and second sets of tomosynthesis projection images then are processed to generate respective first and second tomosynthesis reconstructed image sets of the target volume. Any of a variety of different tomosynthesis reconstruction algorithms may be used including, but not limited to, filtered backprojection (FBP), matrix inversion tomosynthesis (MITS), maximum likelihood expectation maximization (MLEM), and iterative ordered-subset convex (OSC) algorithms based on a maximum-likelihood models.

The first and second tomosynthesis reconstructed image sets then are processed in conjunction with each other on a locationwise basis (e.g., voxelwise basis) within the target volume to generate a dual-energy processed image set. In one embodiment, the processing of the first and second tomosynthesis reconstructed image sets comprises registration (either by a known physical transformation between the imaging coordinate spaces or by image-based registration) and combination processing and/or other decomposition into soft-tissue and bone image components. Treatment radiation is delivered to the treatment target within the target volume based at least in part on the dual-energy processed image set.

Still referring to FIG. 2, computer system 250 is integrated with and/or coupled to IGRT system 200 using one or more buses, networks, or other communications systems 260, including wired and/or wireless communications systems, and being capable in conjunction therewith of implementing the methods of one or more of the preferred embodiments. Methods of image guided radiation treatment in accordance with one or more of the preferred embodiments may be implemented in machine-readable code (i.e., software or computer program product) and performed on computer systems such as, but not limited to, computer system 250. Computer system 250 includes central processing unit (CPU) 251 having microprocessor 252, random access memory 253, and nonvolatile memory 254 (e.g. electromechanical hard drive, solid state drive), display monitor 255, mouse 261, keyboard 263, and other I/O devices 256 capable of reading and writing data and instructions from machine-readable media 258 such as tape, compact disk (CD), digital versatile disk (DVD), blu-ray disk (BD), and so forth. In addition, computer system 250 may be connected via one or more buses, networks, or other communications systems 260 to other computers and devices, such as may exist on a network of such devices, e.g., Internet 259. Software to control the image guided radiation treatment steps described herein may be implemented as a program product and stored on a tangible storage device such as machine-readable medium 258, external nonvolatile memory device 262, cloud storage, or other tangible storage medium.

Figure 3A:
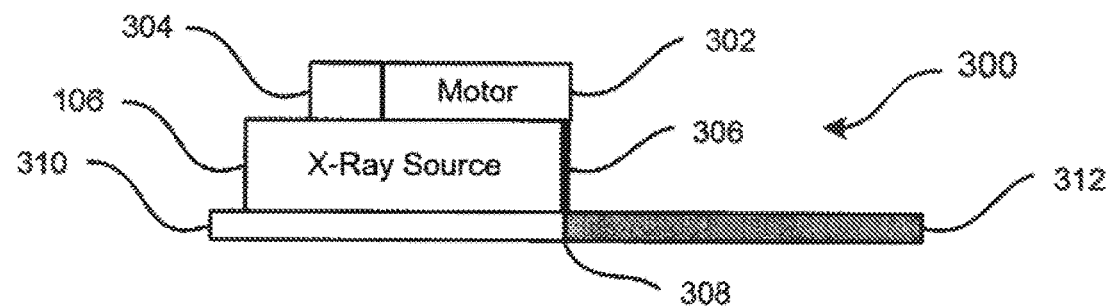
FIGS. 3A and 3B are, respectively, a side view and a plan view of an exemplary x-ray source filter for generating multi-energy x-ray images.
Figure 3B:
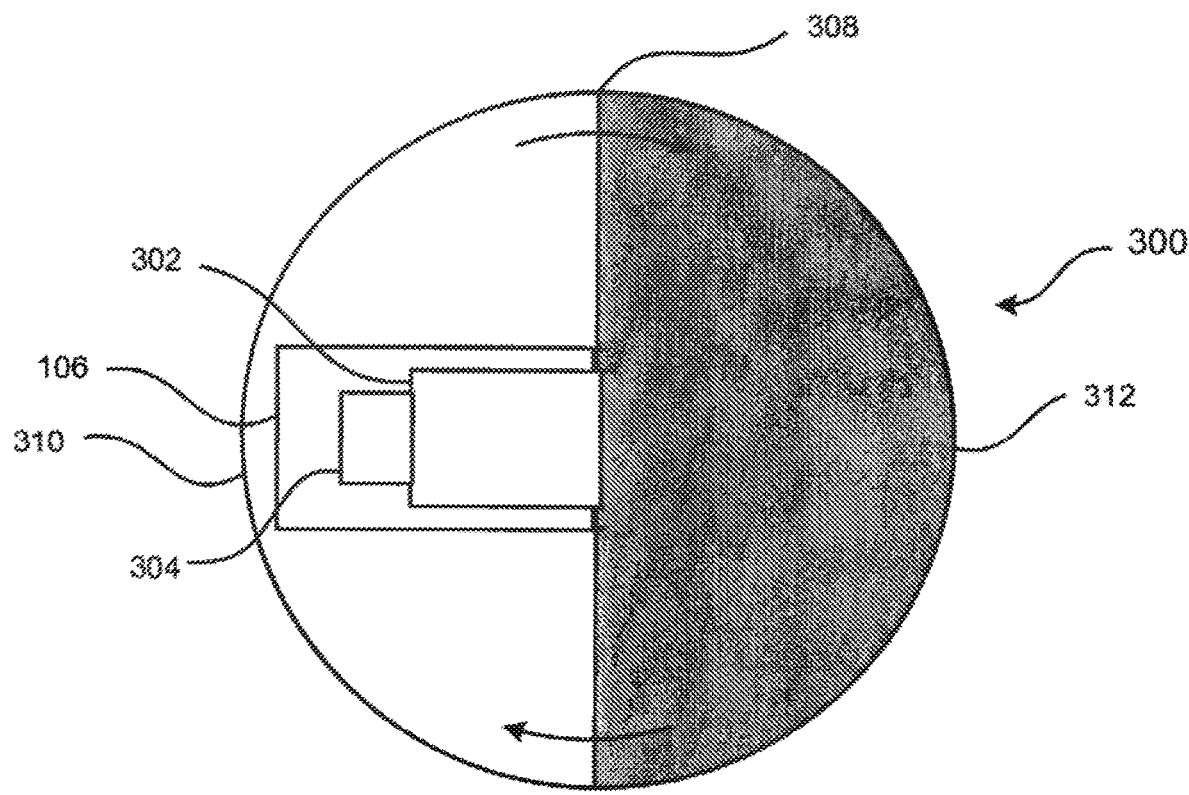

Referring now to FIGS. 3A and 3B, an x-ray source filter for generating multi-energy x-ray images in accordance with the present invention is described. FIGS. 3A and 3B are, respectively, a side view and a plan view of x-ray source filter 300. X-ray source filter 300 includes motor 302, controller 304, shaft 306, and filter material 308. X-ray source filter 300 may be coupled to an x-ray source, e.g., x-ray source 106 of FIG. 1 as illustrated or x-ray sources 108, 206, 208, or any additional x-ray sources provided.

Motor 302 is configured to turn shaft 306 in response to commands from controller 304. Controller 304 communicates with computer system 250 (see FIG. 2) which determines desired motor characteristics, such as power and speed, using suitable software. Computer system 250 then transmits the desired motor characteristics to controller 304 using a wired or wireless communication link.

Shaft 306 is coupled to motor 302 and filter material 308 such that filter material 308 rotates when motor 302 turns shaft 306. Filter material 308 is made of at least two materials suitable for filtering x-ray radiation and is configured to filter imaging radiation emitted from x-ray source 106. Filter material 308 includes first filter material 310 and second filter material 312, wherein first filter material 310 comprises different material from second filter material 312. In a preferred embodiment, first filter material 310 includes aluminum (Al) and second filter material 312 includes copper (Cu).

In operation, x-ray source 106 emits imaging radiation at a first energy level. The x-rays travel through first filter material 310 which filters the imaging radiation such that low energy radiation exits first filter material 310. In response to information transferred from computer system 250, controller 304 commands motor 302 to turn shaft 306 which rotates filter material 308 such that second filter material 312 is positioned adjacent x-ray source 106. Then, x-ray source 106 emits imaging radiation at the same first energy level. The radiation travels through second filter material 312 which filters the imaging radiation such that high energy radiation exits second filter material 312. This process continues such that the energy levels of imaging radiation exiting filter material 308 alternate between low and high energies.

Figure 4A:
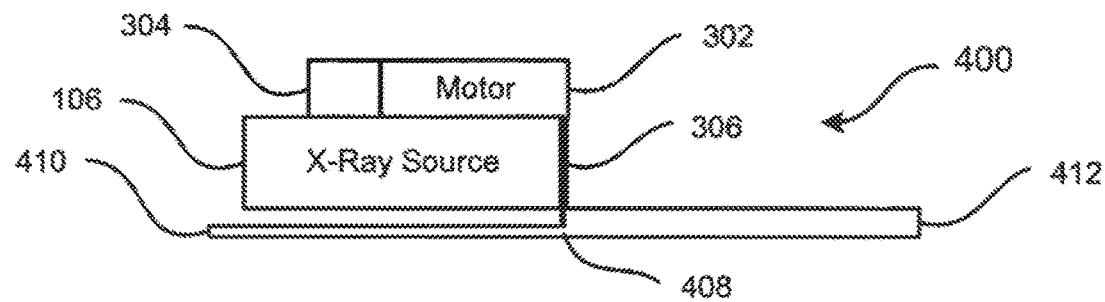
FIGS. 4A and 4B are, respectively, a side view and a plan view of an alternative x-ray source filter for generating multi-energy x-ray images.
Figure 4B:
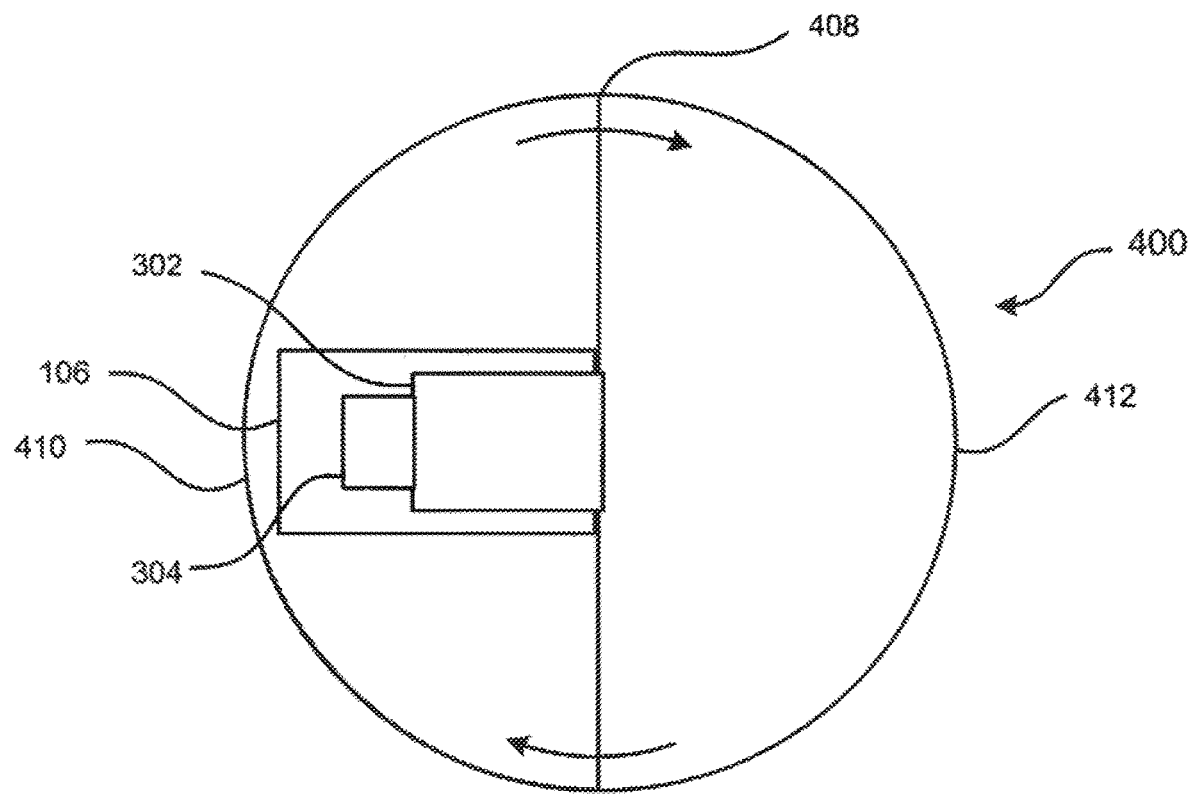

FIGS. 4A and 4B illustrate an alternative embodiment of an x-ray source filter for generating multi-energy x-ray images. X-ray source filter 400 includes motor 302, controller 304, shaft 306, and filter material 408. Motor 302, controller 304, and shaft 306 operate in the same manner as described with respect to FIGS. 3A and 3B. Filter material 408 is made of material suitable for filtering x-ray radiation, e.g., Al or Cu, and is configured to filter radiation emitted from x-ray source 106. Filter material 408 includes first filter thickness 410 and second filter thickness 412, wherein first filter thickness 410 is made of the same material as second filter thickness 412, but has a different thickness. As such, imaging radiation emitted from x-ray source 106 has a first energy after traveling through first filter thickness 410 and has a second energy after traveling through second filter thickness 412.

Figure 5A:
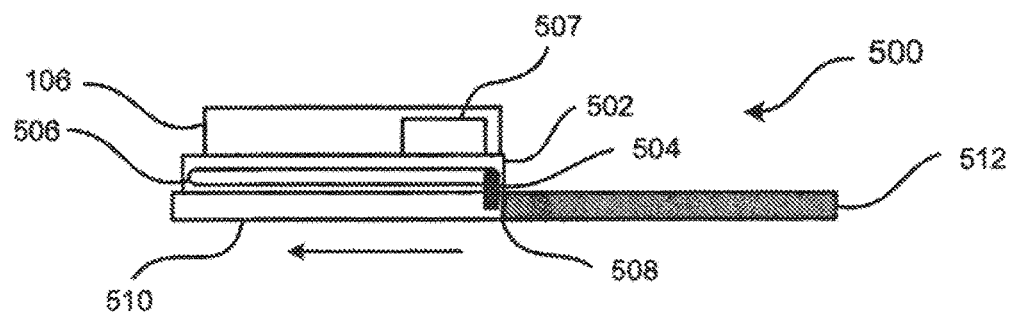
FIG. 5A is a side view of yet another x-ray source filter for generating multi-energy x-ray images.
Figure 5B:
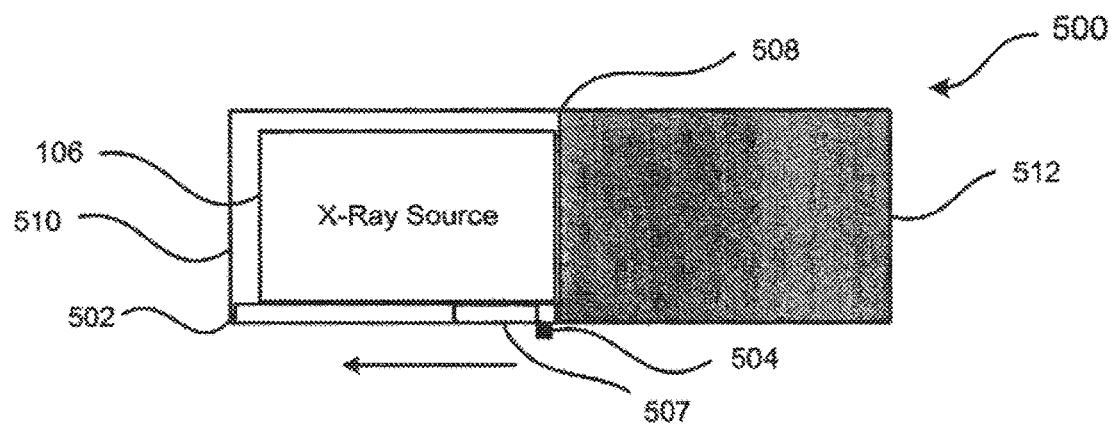
FIG. 5B is a plan view of the x-ray source filter of FIG. 5A at a first position.
Figure 5C:
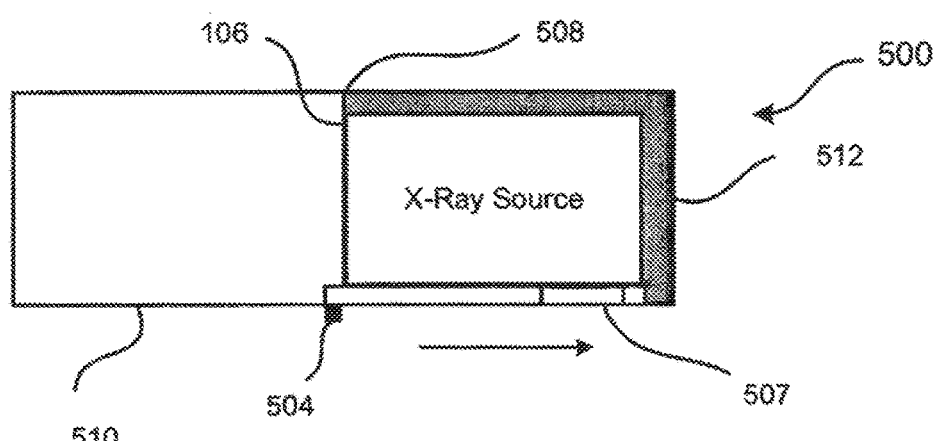
FIG. 5C is a plan view of the x-ray source filter of FIG. 5A at a second position.

Referring now to FIGS. 5A, 5B, and 5C, yet another alternative embodiment of an x-ray source filter for generating multi-energy x-ray images is described. FIG. 5A illustrates a side view of x-ray source filter 500 which includes motor 502, link 504, slot 506, and filter material 508. X-ray source filter 500 is coupled to an x-ray source, e.g., x-ray source 106 of FIG. 1 as illustrated or x-ray sources 108, 206, 208, or any additional x-ray sources provided.

Motor 502 is configured to slide link 504 along slot 506 in response to commands from controller 507. Controller 304 communicates with computer system 250 (see FIG. 2) which determines desired motor characteristics, such as power and speed, using suitable software. Computer system 250 then transmits the desired motor characteristics to controller 304 using a wired or wireless communication link.

Link 504 is coupled to motor 502 and filter material 508 such that filter material 508 translates linearly when motor 502 slides link 504 along slot 506. In one embodiment, filter material 508 is made of at least two materials suitable for filtering x-ray radiation and is configured to filter imaging radiation emitted from x-ray source 106. Filter material 508 includes first filter material 510 and second filter material 512, wherein first filter material 510 comprises different material from second filter material 512. In a preferred embodiment, first filter material 510 includes aluminum (Al) and second filter material 512 includes copper (Cu). In an alternative embodiment, first filter material 510 comprises the same material as second filter material 512, but has a different thickness.

In operation, x-ray source 106 emits imaging radiation at a first energy level when filter material 508 is in a first position as illustrated in FIGS. 5A and 5B. The imaging radiation travels through first filter material 510 which filters the imaging radiation such that low energy radiation exits first filter material 510. In response to information transferred from computer system 250, controller 507 commands motor 502 to slide link 504 along slot 506 which translates filter material 508 to a second position such that second filter material 512 is positioned adjacent x-ray source 106 as illustrated in FIG. 5C. Then, x-ray source 106 emits imaging radiation at the same first energy level. The radiation travels through second filter material 512 which filters the imaging radiation such that high energy radiation exits second filter material 512. This process continues such that the energy levels of imaging radiation exiting filter material 508 alternate between low and high x-ray energies.

As a further alternative, an x-ray source filter may be disposed on a hinge, so that the filter may alternatingly be disposed or removed from the path of imaging radiation emitted by the x-ray source.

In FIGS. 3A-5C, although x-ray source filters 300, 400, and 500 illustratively are separate from x-ray source 106, the filters may be integrated into a common housing with an x-ray source without departing from the scope of the present invention.

Figure 6A:
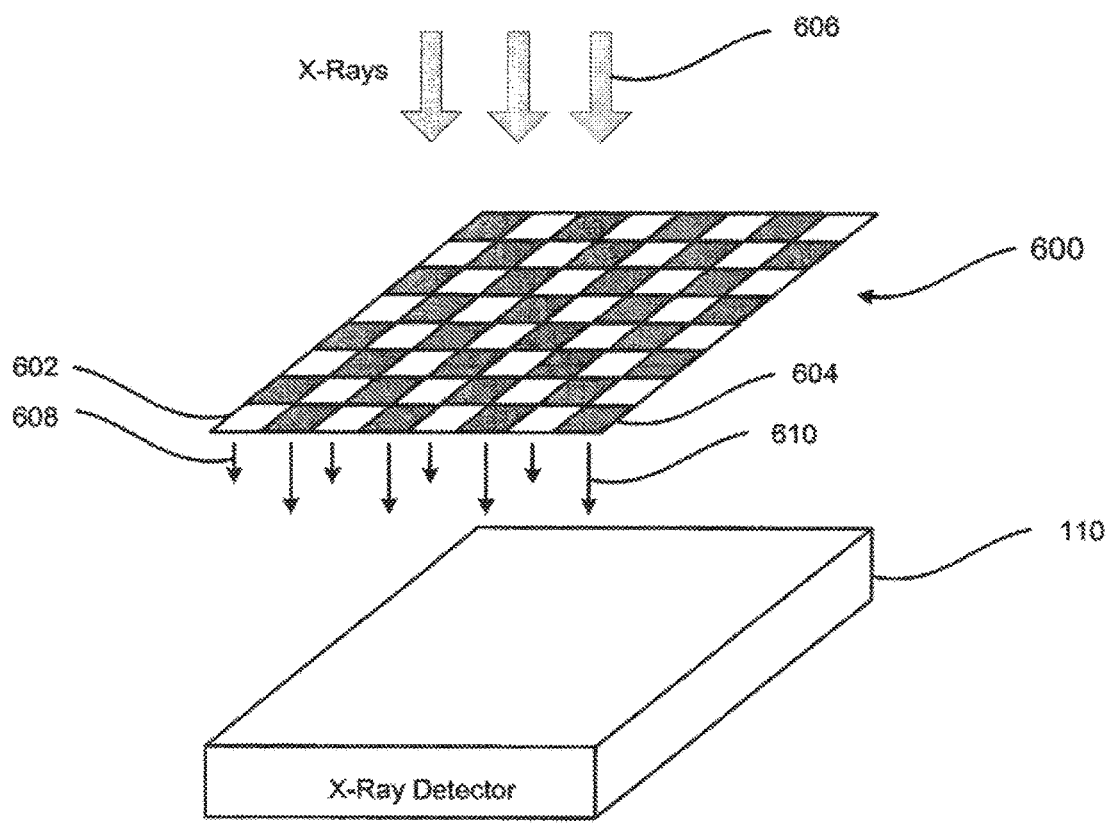
FIGS. 6A and 6B are, respectively, an exploded view and an assembled view of an exemplary x-ray detector filter assembly for generating multi-energy x-ray images.
Figure 6B:
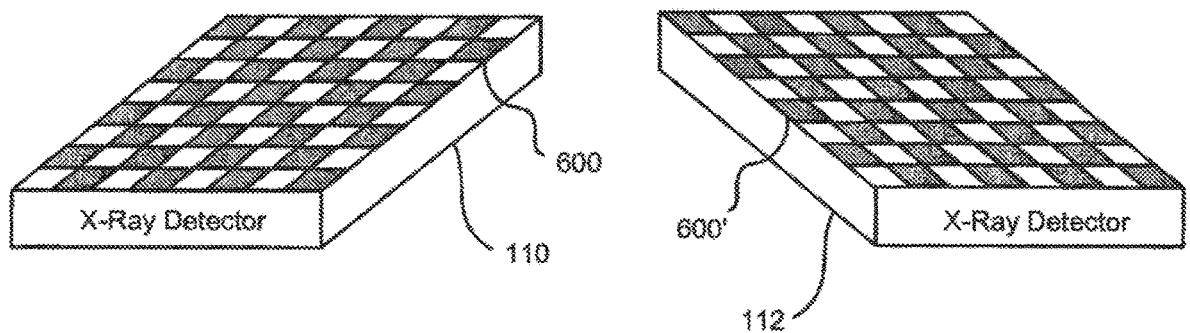

Referring now to FIGS. 6A and 6B, an alternative embodiment is described in which a filter is selectively placed before the detector to filter imaging radiation that has already passed through the patient. In this embodiment, an x-ray detector filter for generating multi-energy x-ray images is described in which x-ray detector filter 600 includes first filter material 602 and second filter material 604. As seen in the exploded view of FIG. 6A and the assembled view of FIG. 6B, x-ray detector filter 600 may be disposed on an x-ray detector, e.g., x-ray detector 110 of FIG. 1 as illustrated or x-ray detector 112, 210, 212, or any additional x-ray detector provided. Alternatively, x-ray detector filter 600 may be integrated into a common housing with an x-ray detector.

X-ray detector filter 600 is made of material suitable for filtering x-ray radiation and is configured to filter imaging radiation, emitted from an x-ray source, that has passed through part or all of a patient. In one embodiment, first filter material 602 comprises different material from second filter material 604. In a preferred embodiment, first filter material 602 includes aluminum (Al) and second filter material 604 includes copper (Cu). In another preferred embodiment, first filter material 602 includes no material and second filter material 604 includes copper (Cu). In an alternative embodiment, first filter material 602 comprises the same material as second filter material 604, but has a different thickness.

In operation, an x-ray source, e.g., x-ray source 106 of FIG. 1, emits x-ray radiation 606 which travel through a patient to x-ray detector filter 600. X-ray radiation 606 passes through first filter material 602 or second filter material 604 of x-ray detector filter 600. First filter material 602 filters x-ray radiation 606 such that low energy x-ray radiation 608 exits first filter material 602 while second filter material 604 filters x-ray radiation 606 such that high energy x-ray radiation 610 exits second filter material 604. Low and high energy x-ray radiations 608 and 610 are received by x-ray detector 110. X-ray detector 110 then transmits the received low and high energy x-ray radiation 608 and 610 to a suitable computer for processing the received radiation into first and second sets of image data and generating multi-energy x-ray images.

X-ray detector filter 600 may take the form of a rectangular grid as illustrated, although many patterns are possible. For example, x-ray detector filter 600 may be patterned such that its columns alternate material or thickness. In a preferred embodiment, first and second filter materials 602 and 604 are each the size of a pixel on x-ray detector 110.

FIG. 6B illustrates an assembled view of an exemplary pair of x-ray detector filters 600 and 600' according to one embodiment of the present invention. X-ray detector filter 600 is disposed on x-ray detector 110 and x-ray detector filter 600' is disposed on x-ray detector 112. X-ray detector filter 600' has a pattern complementary to the pattern of x-ray detector filter 600, for use in stereoscopic imaging. For example, the pattern of x-ray detector filter 600' may mirror the pattern of x-ray detector filter 600 as illustrated.

In FIGS. 3A-6B, although filter materials 308, 408, 508, and x-ray detector filter 600 illustratively include two filter materials or two thicknesses, a greater number of materials and/or thicknesses, e.g., three, four, or more, may be employed to generate x-rays at a greater number of energies, e.g., three, four, or more, without departing from the scope of the present invention.

Systems and Methods for Processing and Using Multi-Energy X-Ray Images

The present invention provides systems and methods for processing multi-energy x-ray images and using the same in image-guided radiation therapy (IGRT). Advantageously, x-rays generated at different energy levels may be processed to generate enhanced image data with positive/negative weight factors from the x-ray images. The enhanced x-ray images may be used for superior target tracking and positioning in IGRT.

Figure 7:
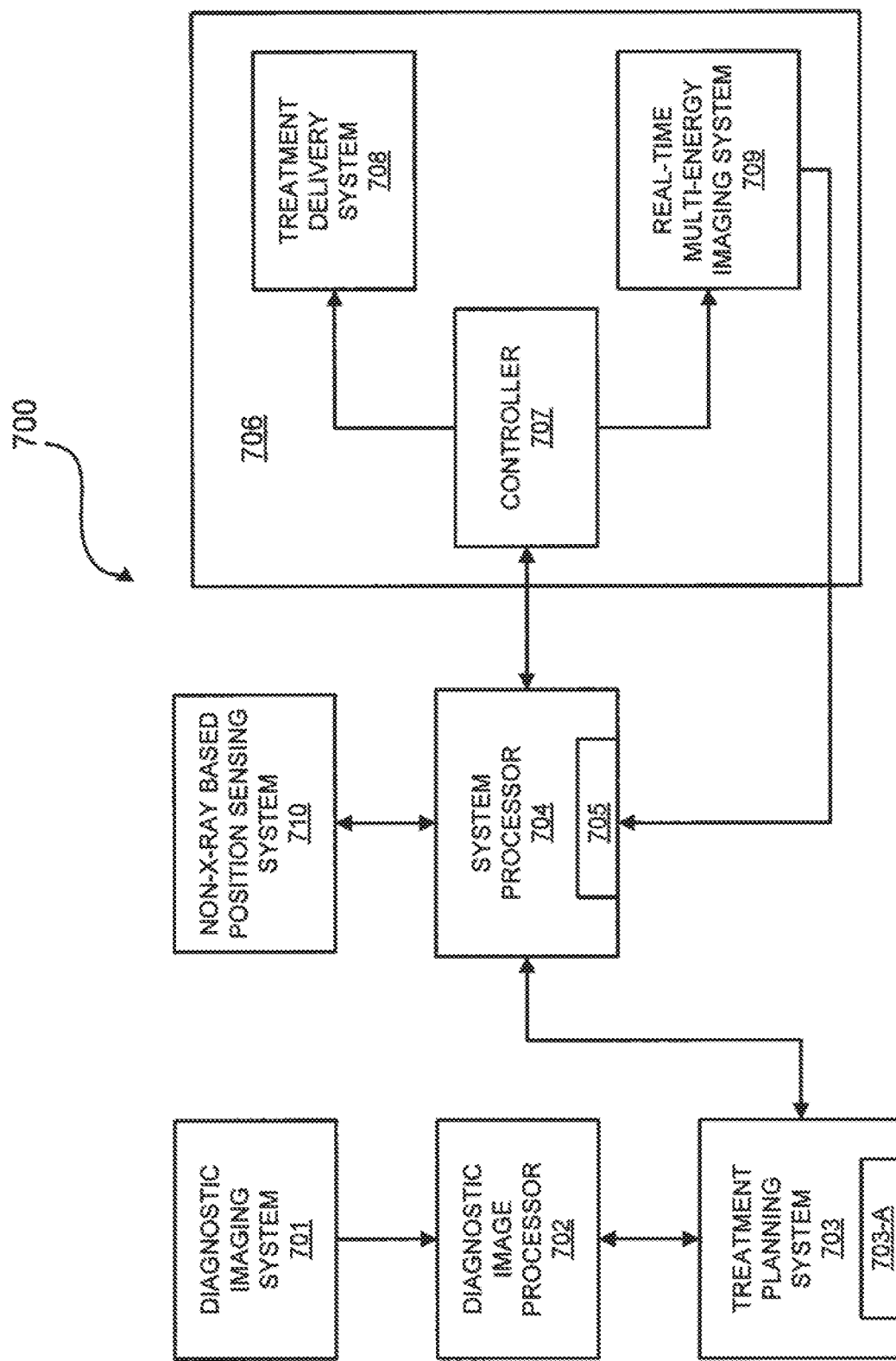
FIG. 7 is a schematic view of an exemplary IGRT system for use with multi-energy x-ray images.

FIG. 7 is a schematic view of an exemplary IGRT system for use with multi-energy x-ray images in accordance with the principles of the present invention. IGRT system 700 may include diagnostic imaging system 701, diagnostic image processor 702, treatment planning system 703, treatment planning library 703-A, system processor 704, memory 705, treatment and imaging system 706, and non-x-ray based position sensing system 710.

Diagnostic imaging system 701 is configured to generate treatment planning images of a region of interest within a patient. Diagnostic imaging system 701 may be a high precision volumetric imaging system such as a computed tomography (CT) system or a nuclear magnetic resonance imaging (MM) system.

Images generated by diagnostic imaging system 701 may be processed to enhance image features by diagnostic image processor 702 using digital enhancement techniques known in the art. Diagnostic image processor 702 may process the images to render digitally reconstructed radiographs (DRRs) using techniques known in the art. The processed images from diagnostic image processor 702 may be stored in treatment planning library 703-A within treatment planning system 703. Treatment planning library 703-A may be any kind of digital storage medium such as, for example, magnetic or solid state media capable of storing digital x-ray images. Treatment planning system 703 may be configured to render 3-D diagnostic images and one or more treatment plans, which treatment plans may include the spatial relationship between a radiation treatment x-ray source and the region of interest during a prospective IGRT procedure. Treatment planning system 703 is coupled to system processor 704 which may be any type of general purpose or special purpose processing device capable of executing instructions and operating on image data and other data, and of commanding an IGRT system, such as treatment and imaging system 706. System processor 704 may include memory 705, which may be any type of memory capable of storing data and instructions for operating IGRT system 700. System processor 704 may be configured to process first and second sets of image data received from real-time multi-energy imaging system 709 to generate an enhanced image of part or all of the patient and to direct treatment delivery system 708 based on information obtained from the enhanced image, as described below.

Treatment and imaging system 706 includes controller 707 coupled to treatment delivery system 708 and real-time multi-energy imaging system 709. Controller 707 may be configured to coordinate the operations of treatment delivery system 708 and real-time multi-energy imaging system 709 in response to commands from system processor 704. Treatment delivery system 708 includes a radiation source configured to generate treatment radiation beams, e.g., x-ray, electron, or proton beams, based on the commands, e.g., a programmed routine, from system processor 704. In one embodiment, treatment delivery system 708 includes articulated robot arm 102, e.g., a six degree-of-freedom robot arm, MV radiation source 104, and treatment table 114 of FIG. 1. In another embodiment, treatment delivery system includes a gantry configured to position the radiation source.

Treatment delivery system 708 may further include a collimator configured to collimate the treatment radiation beams. The collimator may be a fixed collimator, a variable aperture collimator having an aperture, or a multileaf collimator having leaves. In one embodiment, the variable aperture collimator approximates a circular field. System processor 704 may direct treatment delivery system 708 to set the aperture based on information obtained from the enhanced image, to change the diameter of the circular field, to move the leaves of the multileaf collimator, to move the variable aperture collimator, to move the multileaf collimator, and/or to position the patient.

System processor 704 may direct treatment delivery system 708 based on other information obtained from the enhanced image. Such information may include the position of the target within a patient, the position of a skeletal structure within the patient, the position of a soft tissue within the patient, and/or the position of fiducials within the patient and preferably within the target. System processor 704 may direct treatment delivery system 708 to position the radiation source, position the patient using, for example, treatment table 114, and/or enable or disable the treatment radiation beams based on the information.

Real-time multi-energy imaging system 709 is configured to generate two, three, four, or more sets of image data at two, three, four, or more energy levels for generating multi-energy x-ray images of a region of interest that includes the target, the skeletal structure, the soft tissue, and/or fiducials in real-time during an IGRT procedure. The sets of image data may be volumetric image data, such as tomosynthetic image data or CT image data, or a plurality of two-dimensional projection image data. Real-time multi-energy imaging system 709 may include apparatus described above with respect to FIGS. 2-6B for generating multi-energy x-ray images such as x-ray sources 106, 108, 206, 208, x-ray detectors 110, 112, 210, 212, x-ray source filters 300, 400, 500, and/or x-ray detector filter 600, or may include apparatus known to one of ordinary skill in the art for generating multi-energy x-ray images such as a sandwich-type x-ray detector. Real-time multi-energy x-ray images acquired from real-time multi-energy imaging system 709 may be processed by system processor 704 to enhance image features which may improve similarity measures between the pre-treatment and in-treatment images.

Real-time multi-energy imaging system 709 may include an x-ray source array having a plurality of emission spots. A first emission spot of the plurality of emission spots may be configured to emit imaging radiation at the first energy level, and optionally subsequently at the second energy level, and a second emission spot of the plurality of emission spots that may be configured to emit imaging radiation at the second energy level, and optionally subsequently at the first energy level. The plurality of emission spots may be configured to emit imaging radiation at the first energy level and to subsequently emit imaging radiation at the second energy level. The multi-energy imaging system may further include a second x-ray source array having a plurality of emission spots configured to emit imaging radiation in-phase or out of phase with the emission spots of the first x-ray source array. The plurality of emission spots of the first x-ray source array may be configured to emit imaging radiation at the first energy level, and optionally subsequently at the second energy level, and the plurality of emission spots of the second x-ray source array may be configured to emit imaging radiation at the second energy level, and optionally subsequently at the first energy level. The plurality of emission spots of the first x-ray source array and the plurality of emission spots of the second x-ray source array also may be configured to emit imaging radiation at the first energy level and to subsequently emit imaging radiation at the second energy level.

System processor 704 is configured to enhance image features using digital enhancement techniques known in the art. In a preferred embodiment, system processor 704 is configured to combine x-ray images generated at two or more energies to provide multi-energy x-ray images. For example, system processor 704 may combine x-rays generated within a low energy range (e.g., ~50-100 kV) with x-rays generated within a high x-ray energy range (e.g., 100 kV-6 MV, preferably 100-150 kV) to provide enhanced images of objects of interest, e.g., target, soft tissue, and radio-opaque objects such as skeletal structures, fiducials, and contrast agents. System processor 704 may process image data wherein the enhanced image comprises a weighted combination of the first and second sets of image data. The enhanced image may comprise a weighted combination in logarithmic space of the first and second sets of image data and/or a spatially varying weighted combination of the first and second sets of image data. The enhanced image may also be a weighted subtraction in logarithmic space of the first and second sets of image data. The enhanced image may be an x-ray image displaying primarily soft tissue without radio-opaque objects such as skeletal structures, fiducials, and contrast agents. Alternatively, the enhanced image may be an x-ray image displaying primarily radio-opaque objects without soft tissue.

Figure 8A:
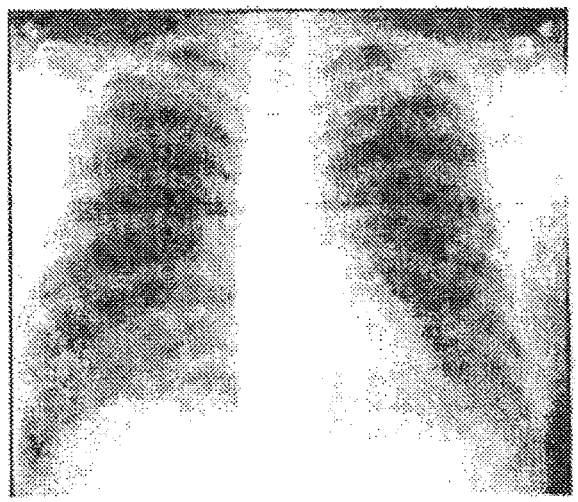
FIGS. 8A and 8B are x-ray images generated by an exemplary real-time multi-energy imaging system.
Figure 8B:
Figure 8C:
FIGS. 8C and 8D are x-rays images processed by an exemplary system processor.
Figure 8D:
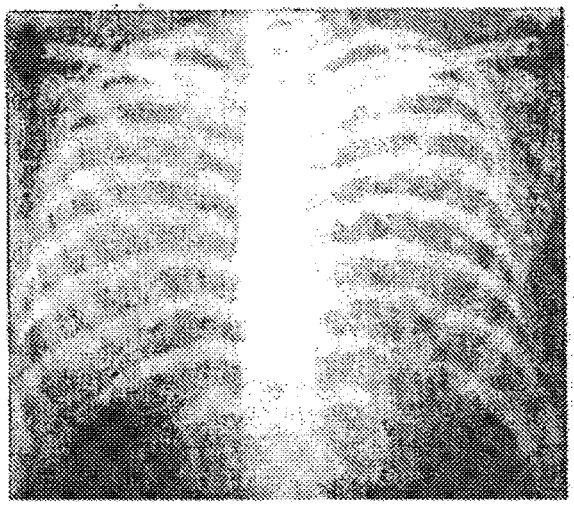

FIGS. 8A and 8B are exemplary x-ray images that may be generated by real-time multi-energy imaging system 709 and FIGS. 8C and 8D are x-rays images that may be processed by system processor 704, available from http://en.wikibooks.org/wiki/Basic_Physics_of_Nuclear_Medicine/Dual-Energy_Absorptiometry. FIG. 8A is a chest x-ray generated at 56 kV, i.e., a low energy x-ray image. FIG. 8B is a chest x-ray generated at 120 kV, i.e., a high energy x-ray image, using a copper filter. FIG. 8C is a processed chest x-ray displaying soft tissue and having the skeletal structures subtracted out. FIG. 8D is a processed chest x-ray displaying skeletal structures and having the soft tissue subtracted out.

Referring back to FIG. 7, registration of the pre-treatment and in-treatment images may be performed by system processor 704 on image data sent to system processor 704 from treatment planning system 703 and real-time imaging system 709. The registration of the pre-treatment and in-treatment x-ray images may include calculation of in-plane translations, in-plane rotation and out-of-plane rotation, as is known in the art.

Non-x-ray based position sensing system 710 is configured to generate a respiratory motion model of a patient. Non-x-ray based position sensing system 710 senses position and/or movement of external marker(s) strategically affixed to the patient, and/or senses position and/or movement of the patient skin surface itself, using one or more methods that do not involve ionizing radiation, such as optically based or ultrasonically based methods. Non x-ray based position sensing system 710 may include external markers affixed in some manner to a patient's chest which move in response to respiration (other mechanisms for monitoring respiration may be used), and include a mono or stereoscopic x-ray imaging system which can precisely determine target location. System 710 correlates motion of the external markers with target motion, as determined from (for example) the mono or stereoscopic x-ray projections. Non x-ray based position sensing system 710 permits system processor 704 to monitor external marker motion, use the correlation model to precisely predict where the target will be located in real time (e.g., ~60 Hz), and direct the treatment beam to the target. As treatment of the moving target progresses, additional x-ray images may be obtained and used to verify and update the correlation model. In one example, non-x-ray position sensing system 710 is similar to SYNCHRONY® Respiratory Tracking System available from Accuray Incorporated of Sunnyvale, California.

Figure 9:
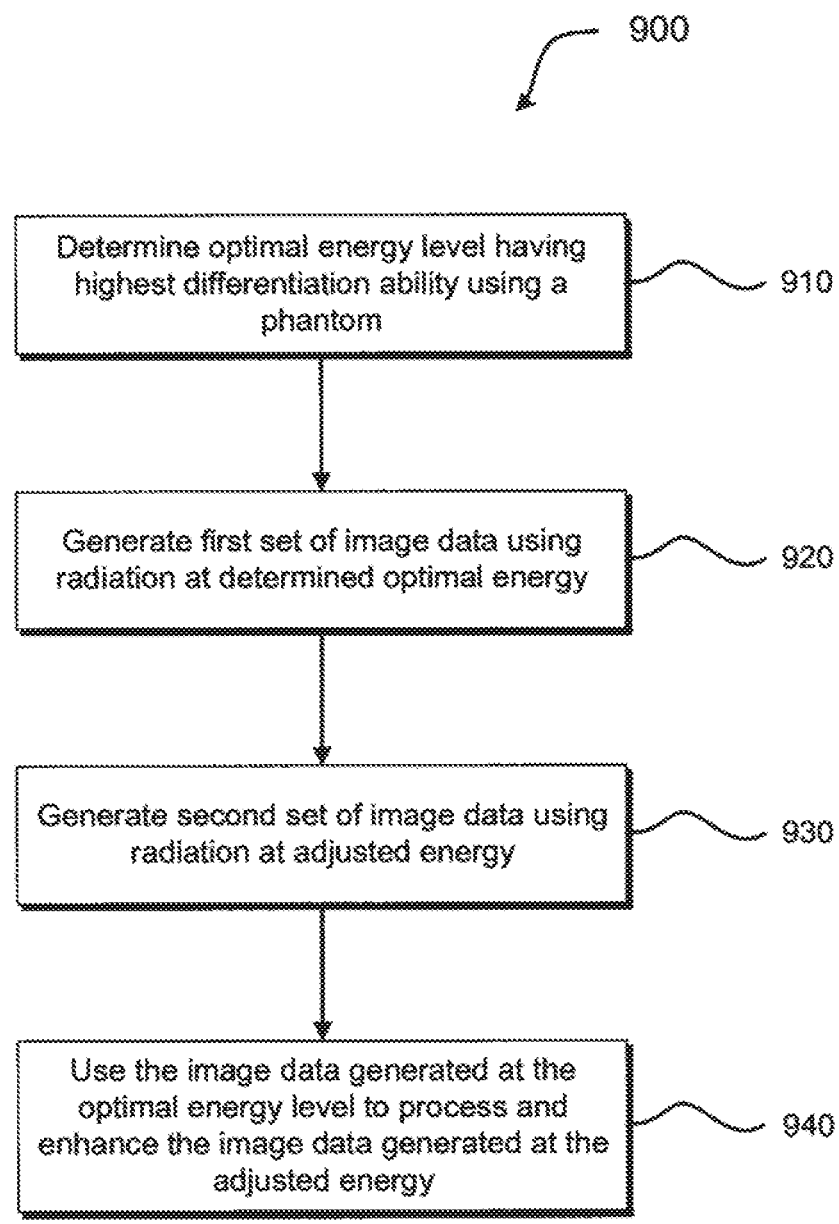
FIG. 9 illustrates an exemplary method for processing multi-energy x-ray image data in IGRT.

FIG. 9 illustrates a method for processing multi-energy x-ray image data in IGRT to enhance image quality in interventional images by exploiting beam hardening effects using High Dynamic Range (HDR) x-ray imaging. With reference to FIG. 7, method 900 may include determining an optimal energy level having the highest definition or differentiation ability for an object of interest, e.g., soft tissue, for imaging the object with real-time multi-energy imaging system 709 using a phantom with system processor 704, at step 910.

Figure 10:
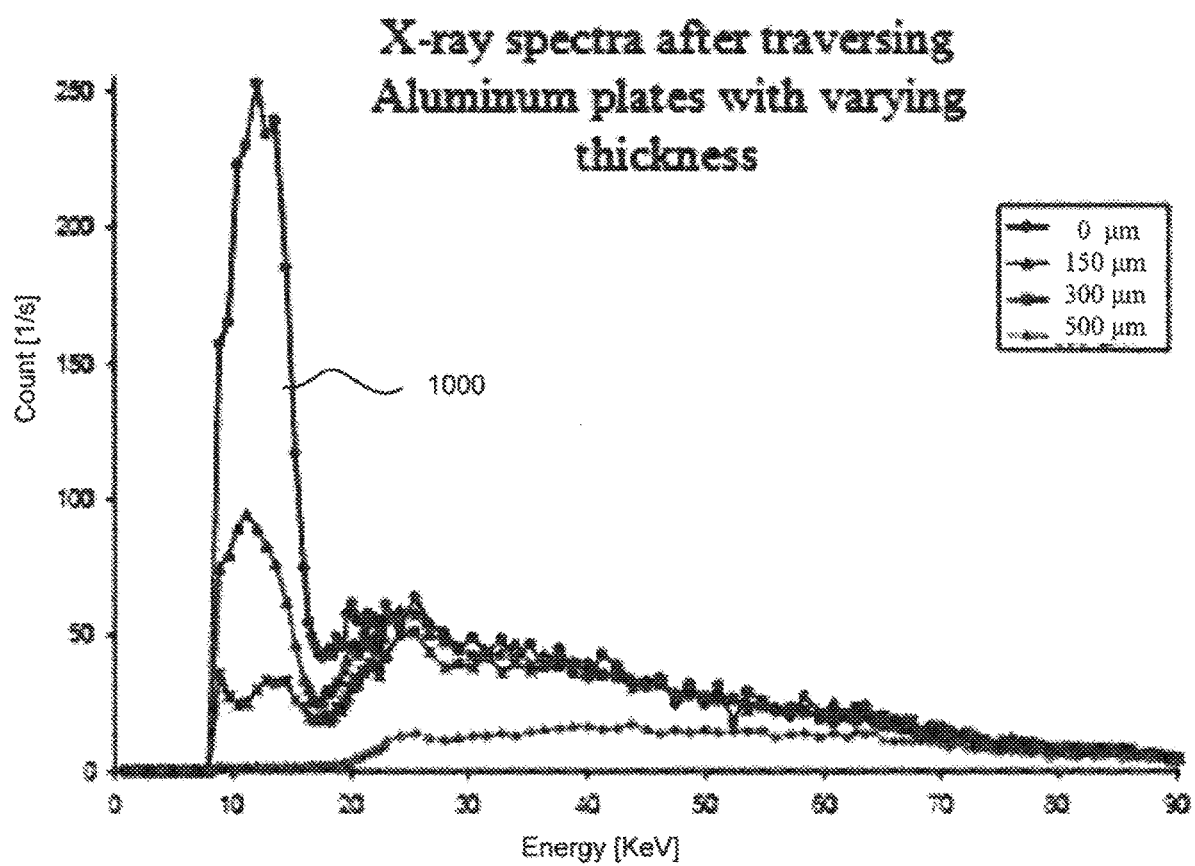
FIG. 10 is a plot illustrating change in x-ray spectra after traversal through a filter for obtaining an optimal energy level.

FIG. 10 is a plot illustrating a change in x-ray spectra after traversal through a filter for determining the optimal energy level. The plot shows count versus energy of x-rays that traversed aluminum plates having varied thickness. X-ray energy level 1000 is the determined optimal energy level for the selected object of interest.

Referring back to FIG. 9, at step 920, a first set of image data is generated using imaging radiation at the optimal energy level with real-time multi-energy imaging system 709. At step 930, the energy of the imaging radiation is adjusted with controller 707 and a second set of image data is generated using imaging radiation at the adjusted energy level with real-time multi-energy imaging system 709. Then, at step 940, the second set of image data generated at the adjusted energy level is processed with the first set of image data generated at the optimal energy level using system processor 704 to generate a processed HDR x-ray image. Advantageously, the processed HDR x-ray image is generated from a combination of x-rays generated over a wide energy spectrum.

Figure 11:
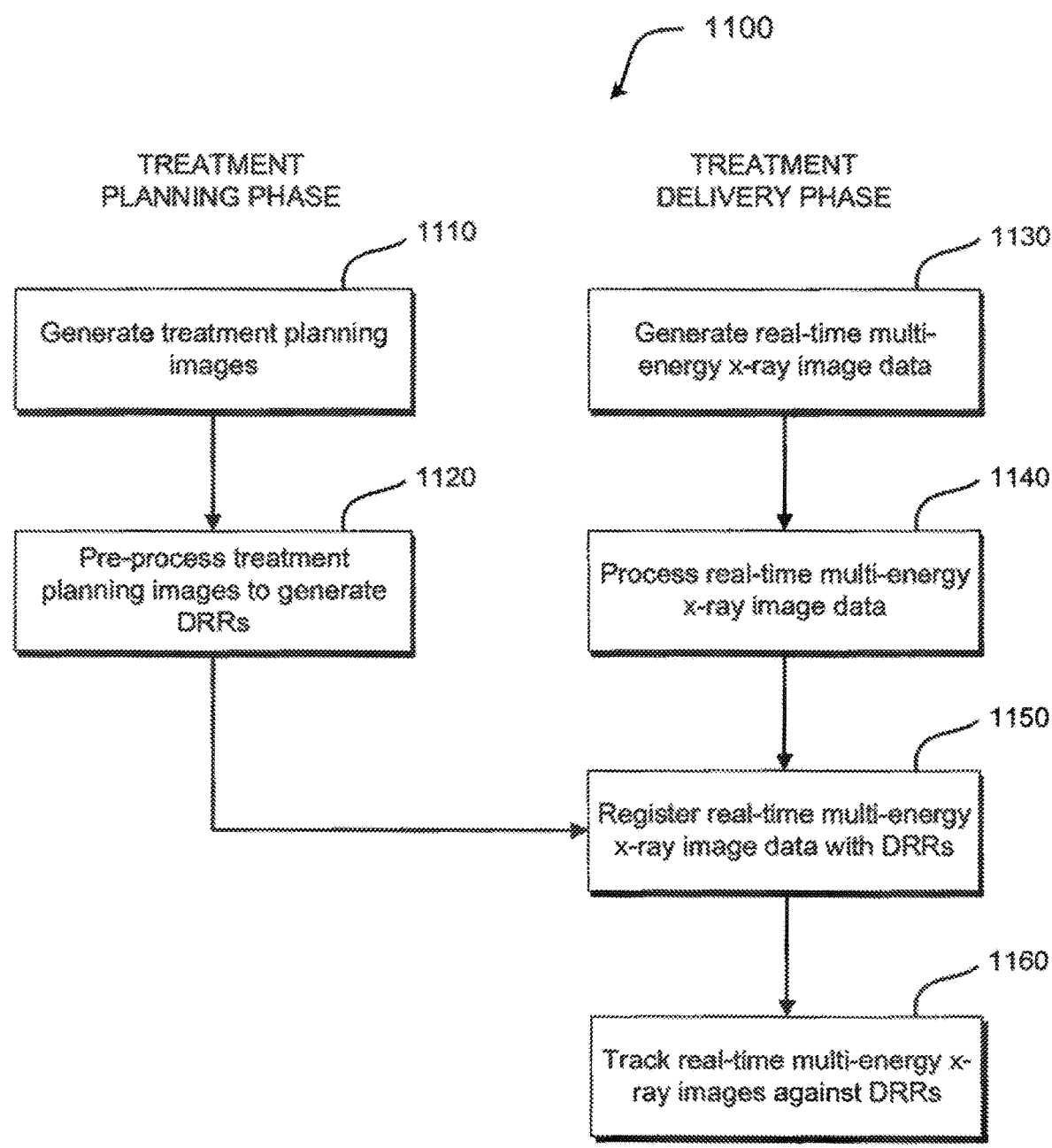
FIG. 11 illustrates an exemplary method for registering multi-energy x-ray images in IGRT.

FIG. 11 illustrates a method for registering multi-energy x-ray images in IGRT in accordance with one aspect of the present invention. With reference to FIG. 7, method 1100 may include, in a treatment planning phase, generating treatment planning images, e.g., a CT volume, with diagnostic imaging system 701 at step 1110. Then, at step 1120, the treatment planning images are pre-processed with diagnostic image processor 702 to generate digitally reconstructed radiographs (DRRs). In a treatment delivery phase, real-time multi-energy x-ray image data is generated with real-time multi-energy imaging system 709 at step 1130. For example, a first set of image data may be generated using imaging radiation at a first energy level and a second set of image data may be generated using imaging radiation at a second energy level. At step 1140, the real-time multi-energy x-ray image data is processed with system processor 704 to extract real-time x-ray image features and to optionally scale the real-time multi-energy x-ray image data to correct for different imaging geometries between diagnostic imaging system 701 and real-time multi-energy imaging system 709. Processing may include combining image data from x-rays generated at different energy levels. At step 1150, the real-time multi-energy x-ray image data is registered with corresponding DRRs with system processor 704 to obtain a registration result. Optionally, at step 1160, the real-time multi-energy x-ray images are tracked against the DRRs with system processor 704 to determine one of interest/patient movement and/or position. Beneficially, tracking the object of interest with multi-energy x-rays images can provide precise target location during IGRT for enhanced accuracy of treatment radiation emission from treatment delivery system 708 to the target.

Figure 12:
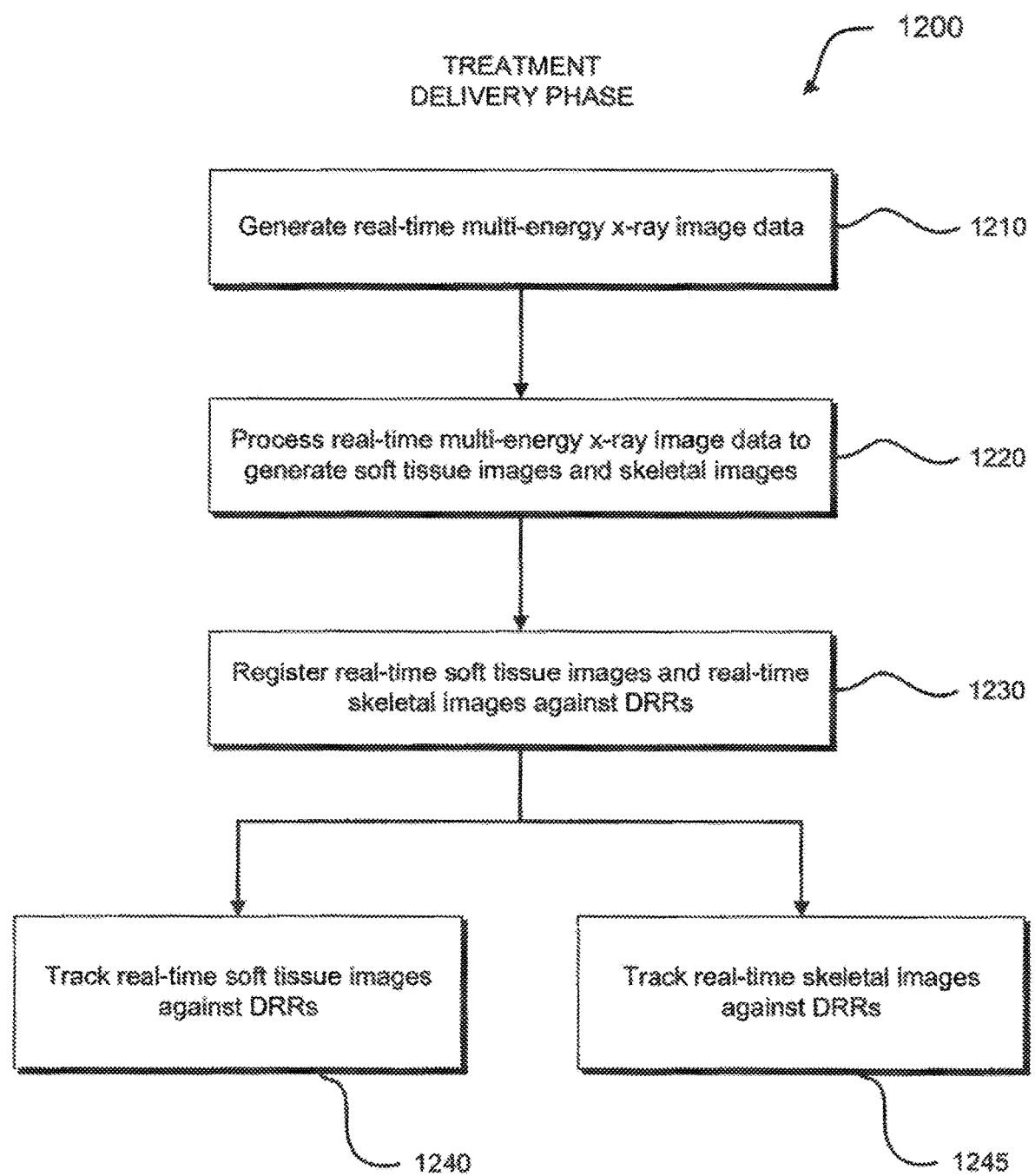
FIG. 12 illustrates an exemplary method for target tracking using multi-energy x-ray images in IGRT.

FIG. 12 illustrates a method for tracking target(s), skeletal structure(s), soft tissue(s), contrast agent(s), fiducial(s), patient movement and/or position using multi-energy x-ray images in IGRT in accordance with another aspect of the present invention. With reference to FIG. 7, method 1200 may include, in a treatment delivery phase, generating real-time multi-energy x-ray image data with real-time multi-energy imaging system 709 at step 1210. For example, a first set of image data may be generated using imaging radiation at a first energy level and a second set of image data may be generated using imaging radiation at a second energy level. Then, at step 1220, the real-time multi-energy x-ray image data is processed with system processor 704 to combine image data from x-rays generated at different energy levels. In a preferred embodiment, system processor 704 processes the multi-energy x-ray image data to combine negative weight factor to subtract radio-opaque objects to generate primarily soft tissue x-ray images and to subtract soft tissues to generate primarily radio-opaque x-ray images. At step 1230, real-time soft-tissue x-ray images are registered with corresponding DRRs with system processor 704 to obtain a soft tissue registration result and real-time radio-opaque object x-ray images are registered with corresponding DRRs with system processor 704 to obtain a radio-opaque registration result. The soft tissue images and/or the radio-opaque object images may be tracked against the DRRs with system processor 704 to determine a target/skeletal structure/soft tissue/fiducial/contrast agent/patient movement and/or position at steps 1240 and 1245.

Advantageously, tracking the target, e.g., a tumor, with soft tissue x-ray images may provide images in which the target is not obscured by overlapping bones, thereby permitting precise determination of the target location during IGRT. In the case where a target is partially or completely blocked by skeletal structures using conventional x-ray images, the soft tissue x-ray images of the present invention may provide a clear target image, allowing for superior target localization and tracking. Moreover, skeletal x-ray images may be used for enhanced patient positioning, e.g., for initial spine alignment, and to track skeletal motion and detect patient shift. Because the techniques of the present invention provide enhanced target/patient movement and/or positioning, the accuracy of treatment radiation emission from treatment delivery system 708 to the target is expected to be superior to previously-known techniques.

Figure 13:
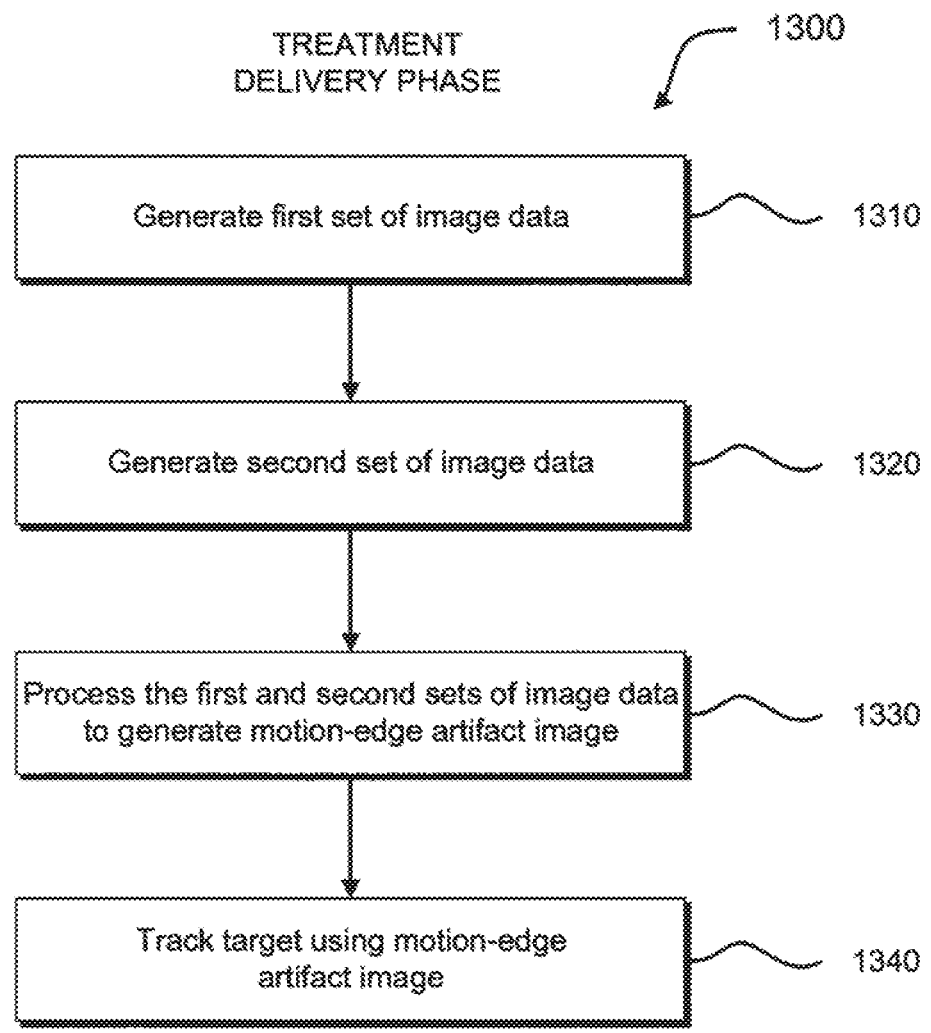
FIG. 13 illustrates an exemplary method for target tracking using a motion-edge artifact in IGRT.

FIG. 13 illustrates a method for target tracking using a motion-edge artifact in IGRT in accordance with yet another aspect of the present invention. With reference to FIG. 7, method 1300 may include, in a treatment delivery phase, generating a first set of image data with real-time multi-energy imaging system 709 at step 1310.

Figure 14A:
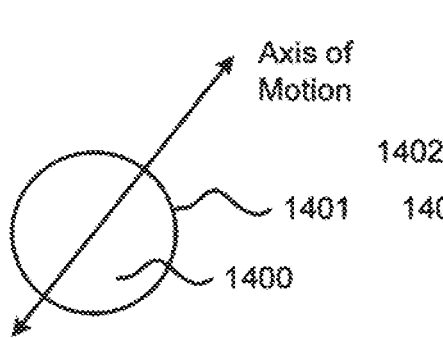
FIGS. 14A and 14B are illustrations of x-ray images of a target at first and second positions, respectively.

FIG. 14A is an illustration of an x-ray image of target 1400 at first position 1401 generated using the first set of image data.

Referring back to FIG. 13, at step 1320, a second set of image data is generated with multi-energy imaging system 709. In a preferred embodiment, the first set of image data is generated using radiation at a first energy level and the second set of image data is generated using radiation at a second energy level.

Figure 14B:
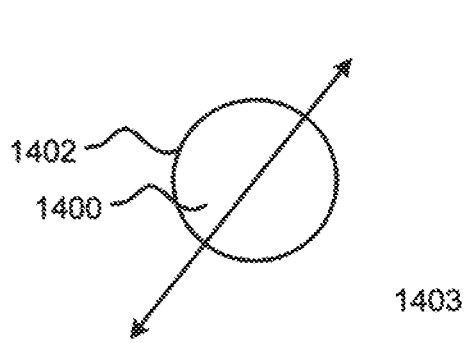

FIG. 14B is an illustration of an x-ray image of target 1400 at second position 1402 generated using second x-ray image data. Illustratively, target 1400 has moved along the Axis of Motion from first position 1401 to second position 1402. Additionally, the Axis of Motion of the target may be estimated from a 4-D CT scan or a 3-D CT inhale/exhale pair during treatment planning with treatment planning system 703.

Again, referring back to FIG. 13, at step 1330, the first and second sets of image data are processed with system processor 704 to perform weighted combination of an overlapping portion of the first and second sets of image data to generate a motion-edge artifact image. Motion artifacts are effects in imaging caused by movement of the target being imaged and are generally seen in images as blurring and/or streaking. The size of the motion artifact may be predicted from a 4-D CT scan because size mostly depends on the dimensions of the target and target velocity in a particular respiratory phase.

Figure 14C:
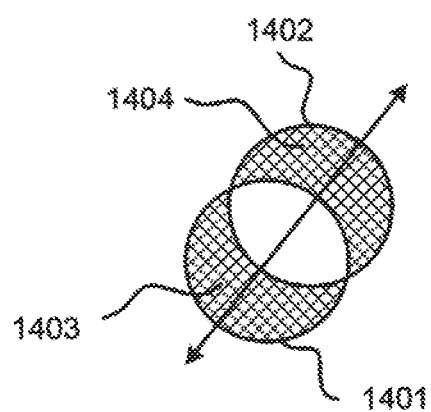
FIG. 14C is an illustration of a motion-edge artifact image generated after subtracting overlapping portions of the target at the first and second positions.

FIG. 14C is an illustration of the motion-edge artifact image generated after combining overlapping portions of the target at first position 1401 and second position 1402. The non-overlapping portions of the target at first and second positions 1401 and 1402 are motion-edge artifacts. Trailing edge artifact 1403 is the area in the x-ray image that was imaged at first position 1401, but not imaged at second position 1402. Leading edge artifact 1404 is the area in the x-ray image that was imaged at second position 1402, but not imaged at first position 1401.

Referring yet again back to FIG. 13, at step 1340, the movement and/or position of the target is tracked with system processor 704 using the motion-edge artifact image which may be inputted into suitable software. In a preferred embodiment, method 1300 is used to track the target, e.g., a tumor. In an alternative embodiment, method 1300 may be used to track non-target structures such as a rib or diaphragm. Advantageously, the methods of the present invention provide enhanced target localization using traditionally unwanted image artifacts as an additional constraint for target localization in IGRT.

Figure 15:
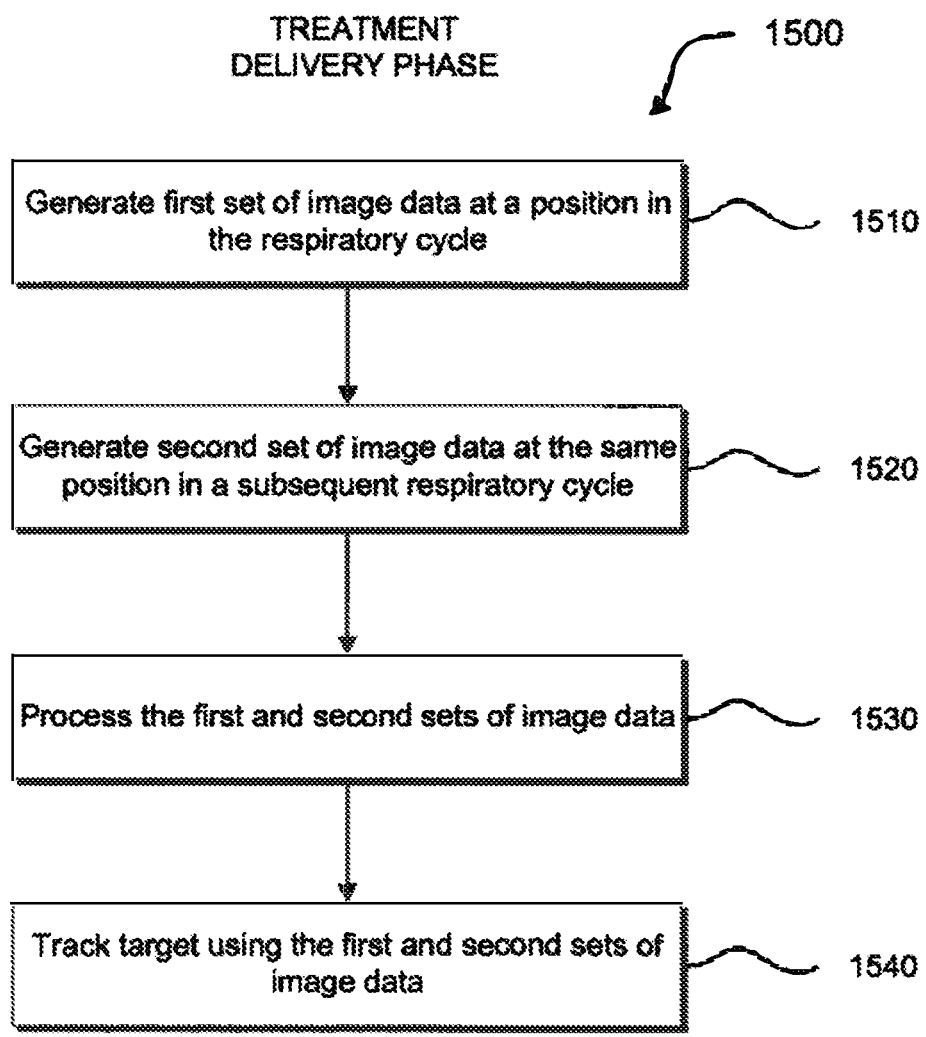
FIG. 15 illustrates a method for target tracking during respiration using multi-energy x-ray images in IGRT.

FIG. 15 illustrates a method for target/soft tissue/skeletal structure/contrast agent/fiducial tracking during respiration using multi-energy x-ray images in IGRT in accordance with the present invention. With reference to FIG. 7, method 1500 may include, in a treatment delivery phase, generating a first set of image data at a position in the patient's respiratory cycle using imaging radiation at a first energy level with real-time multi-energy imaging system 709 at step 1510. At step 1520, a second set of image data is generated at the same position in the patient's subsequent respiratory cycle using imaging radiation at a second energy level with multi-energy imaging system 709. The first and second sets of image data are processed with system processor 704 to predict the target location at different positions in the respiratory cycle at step 1530. System processor 704 may communicate with non-x-ray based position sensing system 710 to enhance the target location prediction based on a respiratory motion model generated by non-x-ray based position sensing system 710. At step 1540, the movement and/or position of the object of interest and/or patient are tracked with system processor 704 using the first and second sets of image data and compared to the predicted target location.

In a preferred embodiment, the first energy level is a high energy level such that the first set of image data includes data having greater soft tissue attenuation and the second energy level is a low energy level such that the second set of image data includes data having greater skeletal structure attenuation. Because soft tissue displacements may vary significantly between respiration cycles due to factors such as tissue hysteresis and variations in alveolar recruitment, skeletal structures may correlate well with the external markers of non-x-ray based position sensing system 710. As such, the first and second sets of image data may be processed to combine the data so that the soft tissue image data is the most recently acquired data and may be used for target tracking and to update the model from non-x-ray based position sensing system 710.

It will be apparent from the foregoing description to one skilled in the art that aspects of the present invention may be embodied, at least in part, in software. That is, referring to FIG. 7, the techniques may be carried out in a computer system or other data processing system in response to its processor, such as system processor 704, executing sequences of instructions contained in a memory, such as memory 705. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as system processor 704 or controller 707.

A machine-readable medium can be used to store software and data which, when executed by a data processing system, causes the system to perform various methods of the present invention. This executable software and data may be stored in various places including, for example, memory 705 and treatment planning library 703-A or any other device that is capable of storing software programs and/or data.

A machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.).

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A method of image-guided radiation, the method comprising:
processing a first set of volumetric image data of a target and a second set of volumetric image data of the target to generate an enhanced image, wherein the first set of volumetric image data and the second set of volumetric image data include an overlapping portion of the target and respective non-overlapping portions of the target, and wherein generating the enhanced image comprises processing the first set of volumetric image data in conjunction with the second set of volumetric image data to perform a weighted combination of the overlapping portion on a voxelwise basis;
registering the enhanced image with another image to obtain a registration result;
tracking the target using the registration result to generate tracking information; and
directing treatment delivery to the target based on the tracking information obtained from the enhanced image.

2. The method of claim 1, wherein the another image comprises a pre-treatment image.

3. The method of claim 1, wherein the first set of volumetric image data and the second set of volumetric image data comprises at least part of the target.

4. The method of claim 1 further comprising generating the first set of volumetric image data of part or all of the target using imaging radiation at a first energy level and the second set of volumetric image data of part or all of the target using imaging radiation at a second energy level.

5. The method of claim 1, wherein the another image comprises a computed tomography (CT) image.

6. The method of claim 1, wherein directing treatment delivery comprises:
generating a treatment delivery beam using a treatment delivery system comprising a radiation source; and
directing the treatment delivery beam to the target based on the tracking information.

7. The method of claim 6, wherein directing treatment delivery comprises adjusting an angle at which the treatment delivery beam is directed to the target.

8. The method of claim 1, wherein directing treatment delivery comprises moving a treatment couch to position the target.

9. The method of claim 1, wherein directing treatment delivery comprises adjusting a collimator to direct a treatment delivery beam to the target based on the tracking information.

10. A system, comprising:
a radiation source;
a processor, operatively coupled with the radiation source, to:
process a first set of volumetric image data of a target and a second set of volumetric image data of the target to generate a combined image, wherein the first set of volumetric image data and the second set of volumetric image data include an overlapping portion of the target and respective non-overlapping portions of the target, and wherein generating the combined image comprises processing the first set of volumetric image data in conjunction with the second set of volumetric image data to perform a weighted combination of the overlapping portion on a voxelwise basis;
register the combined image with another image to obtain a registration result;

track the target using the registration result to generate tracking information; and direct treatment delivery to the target based on the tracking information obtained from the combined image.

11. The system of claim 10, wherein the combined image is an enhanced image.

12. The system of claim 10, further comprising a diagnostic imaging system to acquire the another image.

13. The system of claim 10, wherein to direct treatment delivery, the processor is to:
cause the radiation source to generate a treatment delivery beam; and
direct the treatment delivery beam to the target based on the tracking information.

14. The system of claim 10, further comprising a treatment couch, wherein the processor is operatively coupled with the treatment couch to position the target based on the tracking information.

15. The system of claim 10, further comprising a collimator, wherein the processor is operatively coupled with the collimator to adjust the collimator to direct a treatment delivery beam to the target based on the tracking information.

16. A non-transitory machine readable medium that, when executed by a processor, causes the processor to:
process a first set of volumetric image data of a target and a second set of volumetric image data of the target to generate an enhanced image, wherein the first set of volumetric image data and the second set of volumetric image data include an overlapping portion of the target and respective non-overlapping portions of the target, and wherein generating the enhanced image comprises processing the first set of volumetric image data in conjunction with the second set of volumetric image data to perform a weighted combination of the overlapping portion on a voxelwise basis;
register the enhanced image with another image to obtain a registration result;
track the target using the registration result to generate tracking information; and
direct treatment delivery to the target based on the tracking information obtained from the enhanced image.

17. The non-transitory machine readable medium of claim 16, wherein the another image comprises a pre-treatment image.

18. The non-transitory machine readable medium of claim 16, wherein the processor is further to track information obtained from the enhanced image which comprises a position of the target.

19. The non-transitory machine readable medium of claim 16, wherein to direct treatment delivery, the processor is to:
generate a treatment delivery beam using a treatment delivery system comprising a radiation source; and
direct the treatment delivery beam to the target based on the tracking information.

20. The non-transitory machine readable medium of claim 19, wherein to direct treatment delivery, the processor is further to adjust an angle at which the treatment delivery beam is directed to the target.

21. The non-transitory machine readable medium of claim 16, wherein to direct treatment delivery, the processor is to move a treatment couch to position the target.

22. The non-transitory machine readable medium of claim 16, wherein to direct treatment delivery, the processor is to adjust a collimator to direct a treatment delivery beam to the target based on the tracking information.

* * * * *